United States Patent
Nishide et al.

(10) Patent No.: US 6,770,662 B2
(45) Date of Patent: Aug. 3, 2004

(54) BENZOYLPYRIDINE DERIVATIVE OR ITS SALT, FUNGICIDE CONTAINING IT AS AN ACTIVE INGREDIENT, ITS PRODUCTION PROCESS AND INTERMEDIATE FOR PRODUCING IT

(75) Inventors: Hisaya Nishide, Shiga (JP); Munekazu Ogawa, Shiga (JP); Hidemasa Kominami, Shiga (JP); Koji Higuchi, Shiga (JP); Akihiro Nishimura, Shiga (JP)

(73) Assignee: Ishihara Sangyo Kaisha, Ltd., Osaka (JP)

( * ) Notice: Subject to any disclaimer, the term of this patent is extended or adjusted under 35 U.S.C. 154(b) by 0 days.

(21) Appl. No.: 10/312,040

(22) PCT Filed: Jul. 5, 2001

(86) PCT No.: PCT/JP01/05851
§ 371 (c)(1),
(2), (4) Date: Dec. 23, 2002

(87) PCT Pub. No.: WO02/02527
PCT Pub. Date: Jan. 10, 2002

(65) Prior Publication Data
US 2003/0216444 A1 Nov. 20, 2003

(30) Foreign Application Priority Data

Jul. 5, 2000 (JP) ........................... 2000-203909
Feb. 9, 2001 (JP) ........................... 2001-034182
Mar. 28, 2001 (JP) ........................... 2001-094222

(51) Int. Cl.$^7$ ...................... A61K 31/44; C07D 213/04
(52) U.S. Cl. ...................... 514/354; 546/314; 546/315; 546/298; 546/296; 546/339; 514/355; 514/350; 424/405; 504/254; 504/255
(58) Field of Search ................. 514/354, 355, 514/350; 546/314, 315, 298, 296, 339; 424/405; 504/254, 255

(56) References Cited

U.S. PATENT DOCUMENTS 5,565,413 A * 10/1996 Kanne ..................... 504/254

FOREIGN PATENT DOCUMENTS

| EP | 0 032 516 | 7/1981 |
|---|---|---|
| EP | 0 177 054 | 4/1986 |
| EP | 0 177 907 | 4/1986 |
| EP | 0 704 435 | 4/1996 |
| EP | 0 848 000 | 6/1998 |
| ES | 506 367 | 8/1982 |
| JP | 07 309837 | 11/1995 |
| JP | 2000 063275 | 2/2000 |
| JP | 2001 089412 | 4/2001 |
| WO | 94 24106 | 10/1994 |
| WO | 96 17829 | 6/1996 |
| WO | 98 06700 | 2/1998 |
| WO | 99 41237 | 8/1999 |
| WO | 00 15616 | 3/2000 |

OTHER PUBLICATIONS

Database CA 'Online! Chemical Abstracts Service, Columbus, Ohio, US Anna Arnoldi et al.: "Synthesis of some 3–phenyl–1–substituted(or 1,1–disubstituted)prop–2–yn–1–ols and their in vivo activity against some phytopathogenic fungi" retrieved from STN, database accession No. 99:153745 CA, XP002180437 abstract; RN 87446–23–9.

Masakatsu Sugahara et al.: "A synthesis of 1–pyridylnaphthalene lignan analogs" Tetrahedron Lett., vol. 39, No. 11, pp. 1377–1380 1998.

* cited by examiner

Primary Examiner—Charanjit S. Aulakh
(74) Attorney, Agent, or Firm—Oblon, Spivak, McClelland, Maier & Neustadt, P.C.

(57) ABSTRACT

The present invention relates to a fungicide containing a novel benzoylpyridine derivative or its salt.

The present invention provides a fungicide containing a benzoylpyridine derivative represented by the formula (I) or its salt:

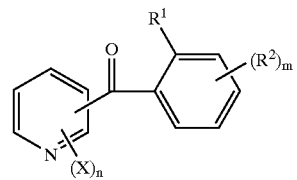

wherein X is a halogen atom, a nitro group, a substitutable alkoxy group, a substitutable aryloxy group, a substitutable cycloalkoxy group, a hydroxyl group, a substitutable hydrocarbon group, a substitutable alkylthio group, a cyano group, a carboxyl group which may be esterified or amidated, or a substitutable amino group; n is 1, 2, 3 or 4; $R^1$ is a substitutable alkyl group; $R^2$ is a substitutable alkyl group, a substitutable alkoxy group, a substitutable aryloxy group, a substitutable cycloalkoxy group or a hydroxyl group; and m is 1, 2, 3 or 4, provided that when m is at least 2, $R^2$ may contain an oxygen atom to form a condensed ring.

18 Claims, No Drawings

BENZOYLPYRIDINE DERIVATIVE OR ITS SALT, FUNGICIDE CONTAINING IT AS AN ACTIVE INGREDIENT, ITS PRODUCTION PROCESS AND INTERMEDIATE FOR PRODUCING IT

TECHNICAL FIELD

The present invention relates to a novel benzoylpyridine derivative or its salt, a fungicide containing it as an active ingredient, its production process and an intermediate for producing it.

BACKGROUND ART

Benzoylpyridine derivatives which are analogous to the compounds of the present invention may be compounds as disclosed in e.g. WO99/41237, WO99/38845, WO96/17829, JP-A-7-309837 and JP-A-2-275858. However, they are different from the compounds of the present invention. Further, the purposes of use of these compounds are different from those of the compounds of the present invention.

Many fungicides which have been conventionally provided have their own characteristics in their controlling effects over pests which cause plant diseases. Some have a slightly poorer curative effect as compared with a preventive effect, and some have a residual effect which lasts only for a relatively short period of time, so that their controlling effects against pests tend to be practically insufficient in some cases. Accordingly, it has been desired to develop a novel compound which has a strong controlling effect against pests which cause plant diseases.

DISCLOSURE OF THE INVENTION

The present inventors have conducted extensive studies to overcome the above problems and as a result, have found that use of the compound represented by the formula (I) as an active ingredient presents excellent preventive effect and curative effect against various plant diseases, particularly powdery mildew of barley, vegetables, fruits and flowering plants, and the present invention has been accomplished.

Namely, the present invention relates to a benzoylpyridine derivative represented by the formula (I) or its salt:

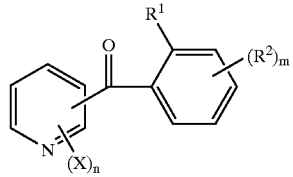

wherein X is a halogen atom, a nitro group, a substitutable alkoxy group, a substitutable aryloxy group, a substitutable cycloalkoxy group, a hydroxyl group, a substitutable hydrocarbon group, a substitutable alkylthio group, a cyano group, a carboxyl group which may be esterified or amidated, or a substitutable amino group; n is 1, 2, 3 or 4; $R^1$ is a substitutable alkyl group; $R^2$ is a substitutable alkyl group, a substitutable alkoxy group, a substitutable aryloxy group, a substitutable cycloalkoxy group or a hydroxyl group; and m is 1, 2, 3 or 4, provided that when m is at least 2, $R^2$ may contain an oxygen atom to form a condensed ring (excluding a case where the pyridine ring is substituted by a benzoyl group at the 2-position; the pyridine ring is substituted by an alkoxy group, a hydroxyl group or a benzyloxy group at the 3-position; and n is 1, m is 1 or 2), a fungicide containing it as an active ingredient, its production process and an intermediate for producing it.

The halogen atom represented by X may, for example, be fluorine, chlorine, bromine or iodine, and preferably fluorine, chlorine or bromine, may, for example, be used.

The alkoxy moiety in the substitutable alkoxy group represented by each of X and $R^2$ may, for example, be a $C_{1-6}$ alkoxy (such as methoxy, ethoxy, propoxy, isopropoxy, butoxy, isobutoxy or t-butoxy), and preferably it may, for example, be a $C_{1-4}$ alkoxy (such as methoxy or ethoxy) Further, the secondary substituent of the substitutable alkoxy group may be from one to five substituents which are the same or different, selected from the group consisting of an aryl, an aryloxy, hydroxyl, nitro, nitroxy, a halogen (such as fluorine, chlorine, bromine or iodine), a haloalkoxy (such as a $C_{1-4}$ haloalkoxy such as $CF_3O$ or $HCF_2O$), a cycloalkyl, amino, an alkylthio and cyano. Of these substitutable alkoxy groups, preferred is an alkoxy group which is not substituted, particularly preferred is a $C_{1-4}$ alkoxy group.

As the aryl moiety in the substitutable aryloxy group represented by X, a condensation type polycyclic group such as naphthyl as well as phenyl may be mentioned, and preferred is phenyl. The secondary substituent of the substitutable aryloxy group may, for example, be a halogen, an alkyl, an alkoxy or hydroxyl. Of these substitutable aryloxy groups, most preferred is a phenoxy group.

The cycloalkyl moiety in the substitutable cycloalkoxy group represented by X is usually one having a carbon number of from 3 to 10, and a monocyclic group such as cyclopropyl, cyclobutyl, cyclopentyl, cyclohexyl or cyclooctyl, as well as a condensation type polycyclic group, may, for example, be mentioned. However, preferred is a monocyclic group. The secondary substituent of the substitutable cycloalkoxy group may, for example, be a halogen, an alkyl, an alkoxy or hydroxyl. Of these substitutable cycloalkoxy groups, most preferred is a cyclohexyloxy group.

The hydrocarbon moiety in the substitutable hydrocarbon group represented by X may, for example, be a $C_{1-6}$ alkyl group (such as methyl, ethyl, propyl, isopropyl, butyl, isobutyl or t-butyl), a $C_{2-6}$ alkenyl (such as vinyl, allyl, isopropenyl or 3-methyl-2-butenyl), a $C_{2-6}$ alkynyl (such as ethynyl, 1-propynyl or 2-propynyl), a $C_{3-6}$ cycloalkyl (such as cyclopropyl, cyclopentyl or cyclohexyl), or a $C_{6-10}$ aryl. Further, the secondary substituent of the substitutable hydrocarbon group may be from one to five substituents which are the same or different, selected from the group consisting of an aryl, an aryloxy, hydroxyl, nitro, nitroxy, a halogen (such as fluorine, chlorine, bromine or iodine), a haloalkoxy (such as a $C_{1-4}$ haloalkoxy such as $CF_3O$ or $HCF_2O$), a cycloalkyl, amino, an alkylthio and cyano. Of these substitutable hydrocarbon groups, preferred is a substitutable alkyl group, and particularly preferred is an alkyl group. Further, a $C_{1-4}$ alkyl group is most preferred among alkyl groups.

The alkylthio moiety in the substitutable alkylthio group represented by X may, for example, be a $C_{1-6}$ alkylthio (such as methylthio, ethylthio, propylthio, isopropylthio, butylthio, isobutylthio or t-butylthio), and preferably a $C_{1-4}$ alkylthio (such as methylthio or ethylthio) may, for example, be mentioned. Of these alkylthio groups which may be substituted, preferred is an alkylthio group, particularly preferred is a $C_{1-4}$ alkylthio group. The secondary substituent of the substitutable alkylthio group may be from one to five substituents which are the same or different, selected from the group consisting of an aryl, an aryloxy, hydroxyl, nitro, nitroxy, a halogen (such as fluorine, chlorine, bromine or iodine), a haloalkoxy (such as a $C_{1-4}$ haloalkoxy such as $CF_3O$ or $HCF_2O$) and cyano.

The carboxyl group which may be esterified or amidated, represented by X, may, for example, be a carboxyl group which may be esterified such as a $C_{1-6}$ alkoxycarbonyl group (such as a methoxycarbonyl group, an ethoxycarbonyl group, a propoxycarbonyl group, an isopropoxycarbonyl group, a butoxycarbonyl group, an isobutoxycarbonyl group or t-butoxycarbonyl group), a nitroxy $C_{1-4}$ alkoxyaminocarbonyl group (such as 2-nitroxyethoxycarbonyl group or a 3-nitroxypropoxycarbonyl group), a phenyl $C_{1-4}$ alkoxycarbonyl group (such as a benzyloxycarbonyl group or a phenethyloxycarbonyl group); or a carboxyl group which may be amidated such as a carbamoyl group, a $C_{1-6}$ monoalkylaminocarbonyl group (such as a methylaminocarbonyl group, an ethylaminocarbonyl group, a propylaminocarbonyl group, an isopropylaminocarbonyl group, a butylaminocarbonyl group, an isobutylaminocarbonyl group or a t-butylaminocarbonyl group), a $C_{1-6}$ dialkylaminocarbonyl group (such as a dimethylaminocarbonyl group, a diethylaminocarbonyl group, a dipropylaminocarbonyl group, a diisopropylaminocarbonyl group, a dibutylaminocarbonyl group or an isobutylaminocarbonyl group), a nitroxy $C_{1-4}$ alkylaminocarbonyl group (such as a 2-nitroxyethylaminocarbonyl group or a 3-nitroxypropylaminocarbonyl group), a phenyl $C_{1-4}$ alkylaminocarbonyl group (such as a benzylaminocarbonyl group or a phenethylaminocarbonyl group), a $C_{3-6}$ cycloalkylaminocarbonyl group (such as a cyclopropylaminocarbonyl group, a cyclopentylaminocarbonyl group or a cyclohexylaminocarbonyl group), a cyclic aminocarbonyl group (such as a morpholinocarbonyl group, a piperidinocarbonyl group, a pyrrolidinocarbonyl group or a thiomorpholinocarbonyl group) or an aminocarbonyl group.

The substitutable amino group represented by X may, for example, be an amino group or an alkylamino group such as a monoalkylamino group or a dialkylamino group. The alkyl moiety in the alkylamino group (a monoalkylamino group or a dialkylamino group) is preferably a $C_{1-4}$ alkyl. The secondary substituent of the substitutable amino group may be from one to five substituents which are the same or different, selected from the group consisting of an aryl, an aryloxy, hydroxyl, nitro, nitroxy, a halogen (such as fluorine, chlorine, bromine or iodine), a haloalkoxy (such as a $C_{1-4}$ haloalkoxy group such as $CF_3O$ or $HCF_2O$), a cycloalkyl, amino, an alkylthio and cyano.

The alkyl moiety in the substitutable alkyl group represented by each of $R^1$ and $R^2$ is preferably a $C_{1-6}$ alkyl (such as methyl, ethyl, propyl, isopropyl, butyl, isobutyl or t-butyl), and among them, preferred is a $C_{1-4}$ alkyl. The secondary substituent of the substitutable alkyl group may be from one to five substituents which are the same or different, selected from the group consisting of an aryl, an aryloxy, hydroxyl, nitro, nitroxy, a halogen (such as fluorine, chlorine, bromine or iodine), a haloalkoxy (such as a $C_{1-4}$ haloalkoxy such as $CF_3O$ or $HCF_2O$), a cycloalkyl, amino, an alkylthio and cyano. Of these substitutable alkyl groups, preferred is an alkyl group which is not substituted, and particularly preferred is a $C_{1-4}$ alkyl group. Among them, most preferred is a methyl group.

The alkoxy moiety in the substitutable alkoxy group represented by $R^2$ is preferably a $C_{1-6}$ (alkoxy such as methoxy, ethoxy, propoxy, isopropoxy, butoxy, isobutoxy or t-butoxy), and among them, preferred is a $C_{1-4}$ alkoxy. The secondary substituent of the substitutable alkoxy group may be from one to five substituents which are the same or different, selected from the group consisting of an aryl group, an aryloxy group, a hydroxyl group, a nitro group, a nitroxy group, a halogen atom (such as fluorine, chlorine, bromine or iodine), a haloalkoxy group (such as a $C_{1-4}$ haloalkoxy group such as $CF_3O$ or $HCF_2O$), a cycloalkyl group, an amino group, an alkylthio group and a cyano group. Of these substitutable alkoxy groups, most preferred is an alkoxy group which is not substituted.

As the aryl moiety in the substitutable aryloxy group represented by $R^2$, a condensation type polycyclic group such as naphthyl, as well as phenyl, may be mentioned, and preferred is phenyl. The secondary substituent of the substitutable aryloxy group may, for example, be a halogen atom, an alkyl group, an alkoxy group or a hydroxyl group. Of these substitutable aryloxy groups, most preferred is a phenoxy group which is not substituted.

The cycloalkyl moiety in the substitutable cycloalkoxy group represented by $R^2$ is usually one having a carbon number of from 3 to 10, and a monocyclic group such as cyclopropyl, cyclobutyl, cyclopentyl, cyclohexyl or cyclooctyl, as well as a condensation type polycyclic group, may, for example, be mentioned, however, preferred is a monocyclic group. The secondary substituent of the substitutable cycloalkoxy group may, for example, be a halogen, an alkyl, an alkoxy or hydroxyl. Of these substitutable cycloalkoxy groups, most preferred is a cyclohexyloxy group which is not substituted.

Here, the aryl moiety, the cycloalkyl group and the alkylthio group in the secondary substituent of the substituent represented by X, $R^1$ and $R^2$ are as defined for the substituents represented by X, $R^1$, $R^2$ and $R^3$.

The compound represented by the formula (I) may form a salt together with an acid substance, and it can form, for example, an inorganic salt such as a hydrochloride, a hydrobromate, a phosphate, a sulfate or a nitrate, or an organic salt such as an acetate, a benzoate, a p-toluenesulfonate, a methanesulfonate or a propanesulfonate.

BEST MODE FOR CARRYING OUT THE INVENTION

Some of the preferred modes of the benzoylpyridine derivative represented by the formula (I) are shown below. These modes may be mutually combined. Further, these compounds are useful as a fungicide.

$R^{2'}$, $R^{2''}$ and $R^{2'''}$ are as defined for the above $R^2$, and $X^1$, $X^2$, $X^3$ and $X^4$ are as defined for the above X.

(1) A benzoylpyridine derivative represented by the formula (I') or its salt:

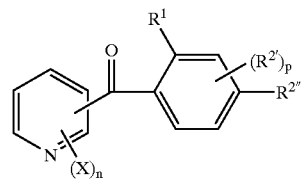

wherein X, n and $R^1$ are as defined in the above general formula (I), $R^{2'}$ is a substitutable alkyl group, a substitutable alkoxy group, a substitutable aryloxy group, a substitutable cycloalkoxy group or a hydroxyl group, p is 1, 2 or 3, and $R_2''$ is a substitutable alkoxy group or a hydroxyl group, provided that at least two of $R^{2'}$ and $R^{2''}$ may contain an oxygen atom to form a condensed ring (excluding a case where the pyridine ring is substituted by a benzoyl group at the 2-position; the pyridine ring is substituted by an alkoxy group, a hydroxyl group or a benzyloxy group at the 3-position; and n is 1, p is 1).

(2) The benzoylpyridine derivative or its salt according to the above item (1), which is represented by the formula (I''):

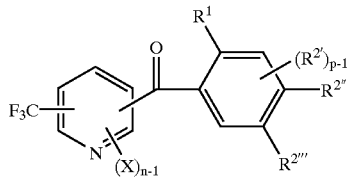

wherein X is a halogen atom, a nitro group, a substitutable alkoxy group, a substitutable aryloxy group, a substitutable cycloalkoxy group, a substitutable hydrocarbon group, a substitutable alkylthio group, a cyano group, a carboxyl group which may be esterified or amidated, or a substitutable amino group; n is 1, 2, 3 or 4; $R^1$ is an alkyl group; $R^{2'}$ is a substitutable alkyl group, a substitutable alkoxy group, a substitutable aryloxy group or a substitutable cycloalkoxy group; p is 1, 2 or 3; and each of $R^{2''}$ and $R^{2'''}$ is a substitutable alkoxy group.

(3) The benzoylpyridine derivative or its salt according to the above item (2), wherein X is a halogen atom, a nitro group, a substitutable alkoxy group, a substitutable cycloalkoxy group, an alkyl group, a substitutable alkylthio group or an amino group.

(4) The benzoylpyridine derivative or its salt according to the above item (3), which is represented by the formula (I''):

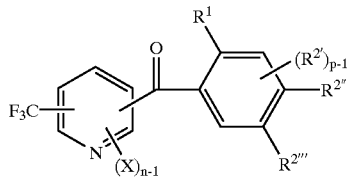

wherein X is a halogen atom, a nitro group, a substitutable alkoxy group, a substitutable cycloalkoxy group, an alkyl group, a substitutable alkylthio group or a substitutable amino group; n is 1, 2, 3, or 4; $R^1$ is an alkyl group; $R^{2'}$ is a substitutable alkyl group, a substitutable alkoxy group, a substitutable aryloxy group or a substitutable cycloalkoxy group; p is 1, 2 or 3; each of $R^{2''}$ and $R^{2'''}$ is a substitutable alkoxy group (excluding a case where the pyridine ring is substituted by a benzoyl group at the 3-position, and the pyridine ring has a $CF_3$ group at at least one of the 2,6-positions).

(5) The benzoylpyridine derivative or its salt according to the above item (1), which is represented by the formula (I'''):

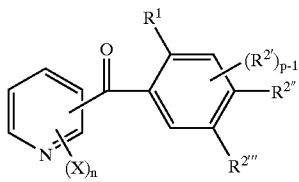

wherein X is a halogen atom, a substitutable alkoxy group, an alkyl group, a $CF_3$ group or an alkylthio group; n is 1, 2, 3 or 4; $R^1$ is an alkyl group; $R^{2'}$ is a substitutable alkyl group, a substitutable alkoxy group or a substitutable cycloalkoxy group; p is 1, 2 or 3; and each of $R^{2''}$ and $R^{2'''}$ is a substitutable alkoxy group.

(6) The benzoylpyridine derivative or its salt according to the above item (5), which is represented by the formula (I'''):

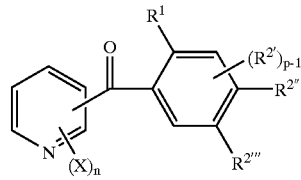

wherein X is a halogen atom, a substitutable alkoxy group, an alkyl group, a $CF_3$ group or an alkylthio group; n is 1, 2, 3, or 4; $R^1$ is an alkyl group; $R^{2'}$ is a substitutable alkyl group, a substitutable aryloxy group or a substitutable cycloalkoxy group; p is 1, 2 or 3; each of $R^{2''}$ and $R^{2'''}$ is a substitutable alkoxy group (excluding a case where the pyridine ring is substituted by a benzoyl group at the 3-position, and the pyridine ring has a $CF_3$ group at at least one of the 2,6-positions).

(7) The benzoylpyridine derivative or its salt according to the above item (5) or (6), wherein the halogen atom represented by X is a fluorine atom or a chlorine atom.

(8) The benzoylpyridine derivative or its salt according to the above item (5) or (6), wherein n is 3 or 4.

(9) The benzoylpyridine derivative or its salt according to the above item (5) or (6), wherein in a case where n is 1 or 2, the halogen atom represented by X is a fluorine atom or a chlorine atom.

(10) The benzoylpyridine derivative or its salt according to the above item (5), which is represented by the formula (I''''):

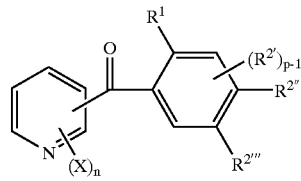

wherein X is a halogen atom, an alkoxy group, an alkyl group, a $CF_3$ group or an alkylthio group; n is 1, 2 or 3; $R^1$ is an alkyl group; $R^{2'}$ is an alkoxy group; p is 1, 2 or 3; and each of $R^{2''}$ and $R^{2'''}$ is an alkoxy group.

(11) The benzoylpyridine derivative or its salt according to the above item (10), which is represented by the formula (I''''):

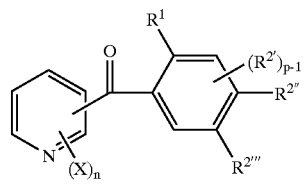

wherein X is a halogen atom, an alkoxy group, an alkyl group, a $CF_3$ group or an alkylthio group; n is 1, 2 or 3; $R^1$ is an alkyl group; $R^{2'}$ is an alkoxy group; p is 1, 2 or 3; and each of $R^{2''}$ and $R^{2'''}$ is an alkoxy group (excluding a case where the pyridine ring is substituted by a benzoyl group at the 3-position, and the pyridine ring has a $CF_3$ group at at least one of the 2, 6-positions).

(12) The benzoylpyridine derivative or its salt according to the above item (8), which is represented by the formula (I'''''):

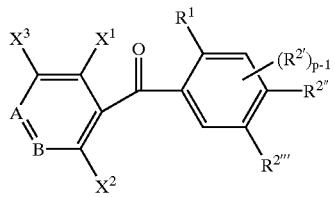

wherein B is —CX⁴= when A is —N=; B is —N= when A is —CH=; each of $X^1$ and $X^2$ which are independent of each other, is a halogen atom, an alkoxy group, an alkyl group, a $CF_3$ group or an alkylthio group; $X^3$ is a hydrogen atom, a halogen atom, an alkoxy group, an alkyl group, a $CF_3$ group or an alkylthio group; $X^4$ is a hydrogen atom, a halogen atom, an alkoxy group, an alkyl group, a $CF_3$ group or an alkylthio group; $R^1$ is an alkyl group; $R^{2'}$ is an alkoxy group; p is 1, 2 or 3; and each of $R^{2''}$ and $R^{2'''}$ is an alkoxy group.

(13) The benzoylpyridine derivative or its salt according to the above item (8), which is represented by the formula (I''''):

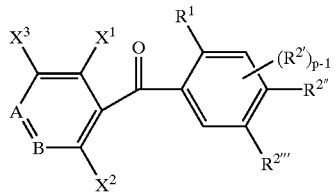

wherein B is —CX⁴= when A is —N=; B is —N= when A is —CH=; each of $X^1$ and $X^2$ which are independent of each other, is a halogen atom, an alkoxy group, an alkyl group, a $CF_3$ group or an alkylthio group; $X^3$ is a hydrogen atom, a halogen atom, an alkoxy group, an alkyl group, a $CF_3$ group or an alkylthio group; $X^4$ is a hydrogen atom, a halogen atom, an alkoxy group, an alkyl group, a $CF_3$ group or an alkylthio group; $R^1$ is an alkyl group; $R^{2'}$ is an alkoxy group; p is 1, 2 or 3; and each of $R^{2''}$ and $R^{2'''}$ is an alkoxy group (excluding a case where A is —CH= and B is —N=, and $X^2$ is a $CF_3$ group).

The compound represented by the formula (I) or its salt may be produced in accordance with a known production process of an analogous compound (such as a process as disclosed in WO96/17829). However, as the preferred modes, Processes 1 to 3 as shown in the following schemes may be mentioned. Here, X, $R^1$, $R^2$, n and m in the formulae are as defined above. One of the substituents represented by $M^1$ in the formula (II) and $M^2$ in the formula (III) is a cyano group, and the other is a metal atom or a composite salt thereof; the substituent represented by W in the formula (V) is a halogen atom or a trifluoromethane sulfonyloxy group; one of the substituents represented by $M^3$ in the formula (VI) and $M^4$ in the formula (VII) is a formyl group, and the other is a metal atom or a composite salt thereof.

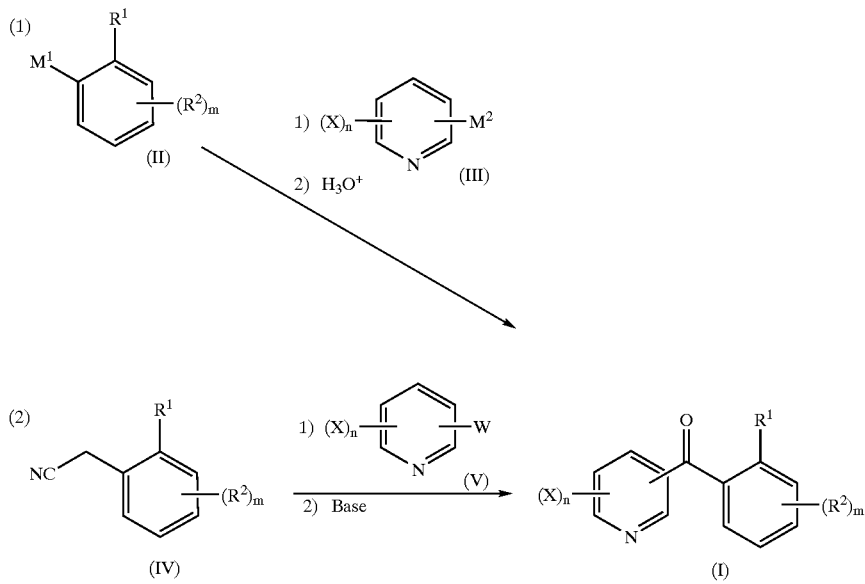

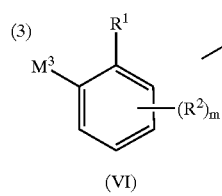
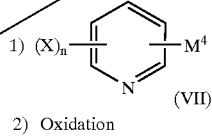

Process 1

A process for producing the compound represented by the formula (I), which comprises subjecting a compound represented by the formula (II) and a compound presented by the formula (III) to a condensation reaction to produce an imine compound represented by the formula (VIII):

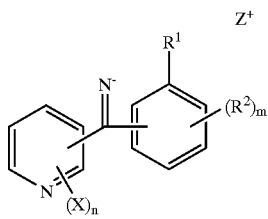

wherein X, $R^1$, $R^2$, n and m are as defined above, and Z is a metal atom or a composite salt thereof, and hydrolyzing it.

The metal atom represented by each of $M^1$ and $M^2$ in the formulae (II) and (III) may, for example, be a typical metal atom such as lithium, magnesium, zinc or copper; or a transition metal atom such as palladium or ruthenium. Further, a composite salt of a metal atom may be used instead of a metal atom.

The compound of the formula (II) wherein $M^1$ is a cyano group and the compound of the formula (III) wherein $M^2$ is a cyano group may be produced in accordance with a known process such as a process as disclosed in Journal of the Chemical Society, Perkin transactions 1 pages 2323–2326, 1999.

The condensation reaction to produce an imine compound is carried out in the presence of a proper solvent (such as an inert solvent such as tetrahydrofuran, diethyl ether, dimethoxyethane, hexane, benzene, toluene or methylene chloride, or a mixed solvent thereof) at a reaction temperature of from −100 to 70° C., preferably from −80 to 30° C. This reaction is carried out preferably in an inert gas atmosphere of e.g nitrogen or argon.

The imine compound produced by the condensation reaction is hydrolyzed by a known procedure and converted into the compound represented by the formula (I). The hydrolysis reaction may be carried out in the presence of e.g. water, an alcohol or a mixture thereof. Here, in Process 1, the condensation reaction and the hydrolysis reaction are usually carried out continuously, and no imine compound is isolated. Further, to obtain the compound represented by the formula (I) with a high yield, it is preferred to carry out the hydrolysis reaction after the condensation reaction is completely conducted.

Process 2

A process for producing the compound represented by the formula (I), which comprises subjecting a compound represented by the formula (IV) and a compound represented by the formula (V) to a condensation reaction to produce a compound represented by the formula (IX):

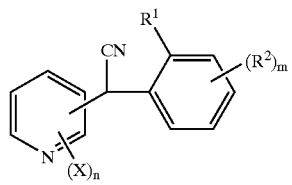

wherein X, $R^1$, $R^2$, n and m are as defined above, and subjecting it to decyanogenation oxidatively in the presence of a base.

The reaction to produce the compound represented by the formula (IX) at the first half stage of Process 2 is carried out usually in the presence of a base preferably in a solvent. The base to be used for the reaction may, for example, be lithium hydride, sodium hydride, sodium methoxide, sodium ethoxide or potassium tert-butoxide. The solvent may, for example, be tetrahydrofuran, diethyl ether, benzene, toluene, methylene chloride, chloroform or DMF, or a mixed solvent thereof. This reaction is carried out preferably at a reaction temperature of from 0 to 100° C. Further, it is carried out preferably in an inert gas atmosphere of e.g. nitrogen or argon. Further, sodium benzenesulfinate or sodium p-toluenesulfinate may be added as the case requires to accelerate the reaction.

The oxidative decyanogenation reaction at the last half stage in Process 2 is carried out in the presence of a base. The base may, for example, be sodium hydride, potassium hydride, sodium carbonate or potassium carbonate. Further, a phase-transfer catalyst (such as benzyl triethylammonium chloride or tetrabutylammonium hydrogensulfate) may be used as the case requires. This reaction is usually carried out in a proper solvent (such as an inert solvent such as methylene chloride, chloroform, 1,2-dichloroethane, benzene, toluene, DMF or DMSO, or a water-containing solvent or a mixed solvent thereof) at a reaction temperature of from 0 to 50° C.

Process 3

A process for producing the compound represented by the formula (I), which comprises reacting a compound represented by the formula (VI) and a compound represented by the formula (VII) to produce phenylpyridyl methanol represented by the formula (X):

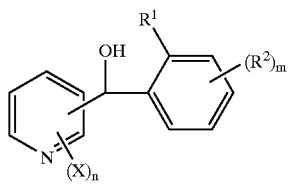

(wherein X, n, m, $R^1$ and $R^2$ are as defined above with a proviso as in formula (I)) and oxidizing it.

Each of metal atoms represented by $M^3$ and $M^4$ in Process 3, may, for example, be a typical metal atom such as lithium, magnesium, zinc or copper; or a transition metal atom such as palladium or ruthenium. Further, a composite salt of a metal atom may be used instead of a metal atom.

The compound of the formula (VI) wherein the substituent represented by $M^3$ is a formyl group and the compound of the formula (VII) wherein the substituent represented by $M^4$ is a formyl group, may usually be produced in accordance with a known process such as a process as disclosed in Journal of Organic Chemistry vol. 57, pages 6847–6852, 1992.

The phenylpyridyl methanol represented by the formula (X), formed from the compound represented by the formula (VI) and the compound represented by the formula (VII), may be oxidized by a known means such as a metal oxidizing agent such as manganese dioxide or chromic acid, a Swern oxidation method (dimethylsulfoxide+oxalyl chloride) or a ruthenium oxidation method (tetrapropylammonium perruthenate+N-methylmorpholine-N-oxide) and converted to a compound represented by the formula (I)

Now, mode of carrying out Process 3 is described below.

(1) A process for producing the compound represented by the formula (I), which comprises reacting a substituted benzaldehyde represented by the formula (VI-1):

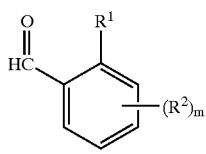

(wherein $R^1$, $R^2$ and m are as defined above), and a metal salt of a substituted pyridine derivative represented by the formula (VII-1):

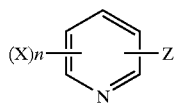

(wherein X is as defined above, and Z is a metal atom or a composite salt thereof), to produce phenylpyridyl methanol represented by the formula (X), and oxidizing it.

(2) A process for producing the compound represented by the formula (I), which comprises reacting a metal salt of a substituted benzene derivative represented by the formula (VI-2):

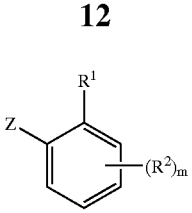

(wherein $R^1$, $R^2$ and m are as defined above, and Z is a metal atom or a composite salt thereof), and a substituted pyridylaldehyde represented by the formula (VII-2):

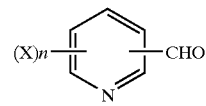

(wherein X is as defined above), to produce phenylpyridyl methanol represented by the formula (X), and oxidizing it.

Here, the preferred modes of the phenylpyridyl methanol represented by the formula (X) which is an intermediate for production of the compound represented by the formula (I) are shown below.

(1) Phenylpyridyl methanol represented by the formula (X'):

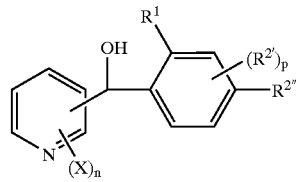

wherein X, n and $R^1$ are as defined for the above general formula (I), $R^{2'}$ is a substitutable alkyl group, a substitutable alkoxy group, a substitutable aryloxy group, a substitutable cycloalkoxy group or a hydroxyl group, p is 1, 2 or 3; and $R^{2''}$ is a substitutable alkoxy group or a hydroxyl group, provided that at least two of $R^{2'}$ and $R^{2''}$ may contain an oxygen atom to form a condensed ring (excluding a case where the pyridine ring is substituted by a benzoyl group at the 2-position; the pyridine ring is substituted by an alkoxy group, a hydroxyl group or a benzyloxy group at the 3-position; and n is 1, p is 1).

(2) The phenylpyridyl methanol according to the above item (1), which is represented by the formula (X''):

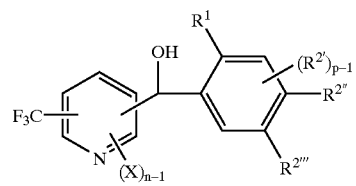

wherein X is a halogen atom, a nitro group, a substitutable alkoxy group, a substitutable aryloxy group, a substitutable cycloalkoxy group, a substitutable hydrocarbon group, a substitutable alkylthio group, a cyano group, a carboxyl group which may be esterified or amidated, or a substitutable amino group; n is 1, 2, 3 or 4; $R^1$ is an alkyl group; $R^{2'}$ is a substitutable alkyl group, a substitutable alkoxy group, a substitutable aryloxy group or a substitutable cycloalkoxy group, p is 1, 2 or 3, and each of $R^{2''}$ and $R^{2'''}$ is a substitutable alkoxy group.

(3) The phenylpyridyl methanol according to the above item (2), wherein X is a halogen atom, a nitro group, a substitutable alkoxy group, a substitutable cycloalkoxy group, an alkyl group, a substitutable alkylthio group or a substitutable amino group.

(4) The phenylpyridyl methanol according to the above item (2) or (3), wherein the pyridine ring is substituted by a benzoyl group at the 4-position.

(5) The phenylpyridyl methanol according to the above item (1), which is represented by the formula (X'''):

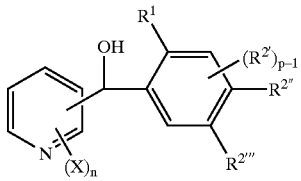

wherein X is a halogen atom, a substitutable alkoxy group, an alkyl group, a $CF_3$ group or an alkylthio group; n is 1, 2, 3 or 4; $R^1$ is an alkyl group; $R^{2'}$ is a substitutable alkyl group, a substitutable alkoxy group or a substitutable cycloalkoxy group; p is 1, 2 or 3; and each of $R^{2''}$ and $R^{2'''}$ is a substitutable alkoxy group.

(6) The phenylpyridyl methanol according to the above item (5), which is represented by the formula (X''''):

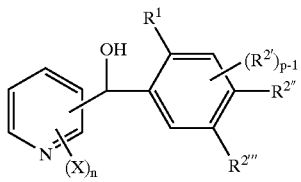

wherein X is a halogen atom, an alkoxy group, an alkyl group, a $CF_3$ group or an alkylthio group; n is 1, 2 or 3; $R^1$ is an alkyl group; $R^{2'}$ is an alkoxy group; p is 1, 2 or 3; and each of $R^{2''}$ and $R^{2'''}$ is an alkoxy group.

(7) The phenylpyridyl methanol according to the above item (5) or (6), wherein the pyridine ring is substituted by a benzoyl group at the 4-position.

(8) The phenylpyridyl methanol according to the above item (6), which is represented by the formula (X'''''):

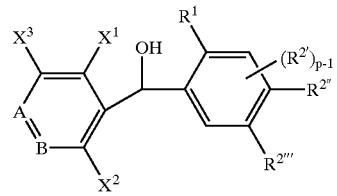

wherein B is $-CX^4=$ when A is $-N=$; B is $-N=$ when A is $-CH=$; each of $X^1$ and $X^2$ which are independent of each other, is a halogen atom, an alkoxy group, an alkyl group, a $CF_3$ group or an alkylthio group; $X^3$ is a hydrogen atom, a halogen atom, an alkoxy group, an alkyl group, a $CF_3$ group or an alkylthio group; $X^4$ is a hydrogen atom, a halogen atom, an alkoxy group, an alkyl group, a $CF_3$ group or an alkylthio group; $R^1$ is an alkyl group; $R^{2'}$ is an alkoxy group; p is 1, 2 or 3; and each of $R^{2''}$ and $R^{2'''}$ is an alkoxy group.

(9) The phenylpyridyl methanol according to the above item (8), wherein A is $-N=$.

A substituent may further be introduced into the compound represented by the formula (I) electrophilically or nucleophilically. That is, the compound represented by the formula (I) may be converted into a compound represented by the formula (I-a) or (I-b) as illustrated in the following scheme. Further, it is also possible to radically introduce a substituent into the compound represented by the formula (I). Here, in the formula (I-a), E is an electrophilic reagent, and in the formula (I-b), Nu is a nucleophilic reagent.

n' and n'' are as defined for the above n.

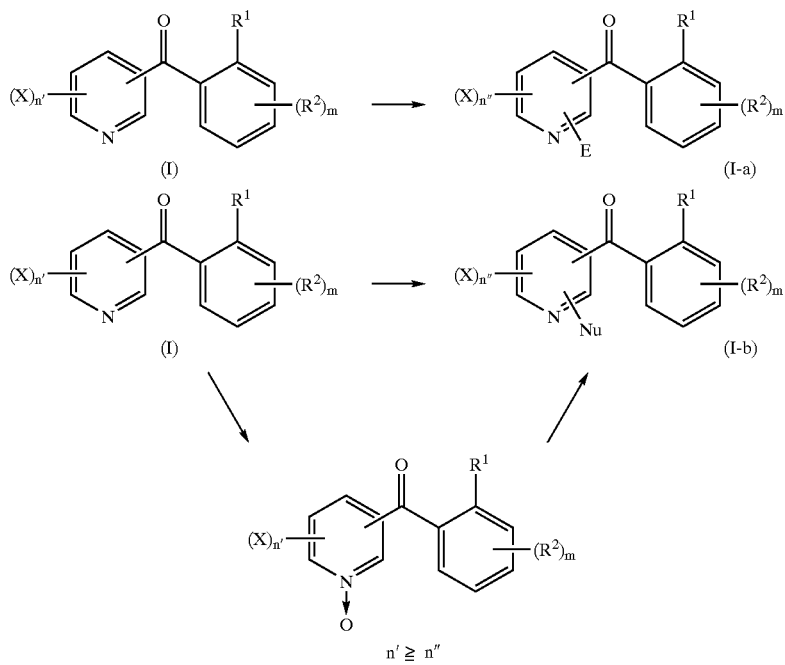

The reaction to prepare the compound represented by the formula (I-a) varies properly depending upon the electrophile, and the reaction may usually be carried out by a known process or a process in accordance therewith. For example, the above-described Process 1 may be employed. The nucleophilic substitution to prepare the compound represented by the formula (I-b) varies properly depending upon the nucleophile, and the reaction may usually be carried out by a known process or a process in accordance therewith. For example, in a case of an ethyloxy nucleophilic reagent, it is preferred to carry out the reaction in the presence of an inert solvent such as ethanol or dioxane, toluene or octane as the solvent, at a reaction temperature of from 0 to 120° C. for a proper time. The ethyloxy nucleophilic reagent is used in from 0.1 to 10 mol equivalent amount, preferably in from 0.5 to 5 mol equivalent amount.

Further, the compound represented by the formula (I-c) (the compound of the formula (I) wherein X is a halogen atom) may further be converted into a compound represented by the formula (I-d) by removing the halogen substituent, as shown in the following scheme. For the reaction as illustrated by the scheme, catalytic hydrogenation, hydrogen transfer reaction or metal reduction reaction may properly be employed. In the scheme, Hal is a halogen atom.

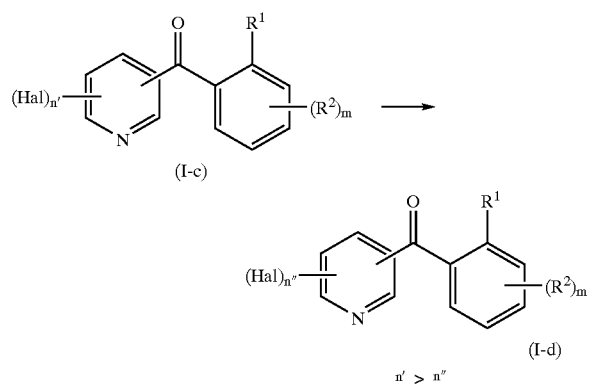

The catalytic hydrogenation may be carried out in the presence of a catalyst under hydrogen gas atmosphere under normal pressure or under elevated pressure in the presence of a proper solvent. The catalyst to be used may, for example, be a catalyst system having platinum, palladium, rhodium, ruthenium, nickel or iridium. The solvent to be used may, for example, be water, an alcohol (such as methanol or ethanol), ethyl acetate, acetic acid, dioxane, ether, benzene or hexane. In such a case, the catalyst is used in a proportion of from 0.01 to 1.2 mol based on the compound represented by the formula (I-c). Further, the reaction may be carried out in the presence of a base such as triethylamine or sodium hydrogen carbonate. Further, a known reduction reaction may be employed such as hydrogen transfer reaction (e.g. palladium carbon, ammonium formate as a hydrogen source, or sodium dihydrogen phosphate) or a metal reduction reaction (e.g. samarium diiodide).

Now, specific Synthesis Examples of the benzoylpyridine derivative represented by the formula (I) and the intermediate for its production are described below (the compounds in Synthesis Examples are based on IUPAC nomenclature, and the substitution positions may be different from those shown in Tables as mentioned hereinafter, expediently).

SYNTHESIS EXAMPLE 1
Synthesis of 3-(2,3,4-trimethoxy-6-methylbenzoyl)-2,6-dichloro-4-trifluoromethylpyridine (compound No. 3)

(a) 14 ml (20 mmol) of n-butyllithium (1.5 M hexane solution) was dropwise added at 0° C. to a solution having 2.9 ml (21 mmol) of diisopropylamine dissolved in 62 ml of tetrahydrofuran, followed by stirring for 30 minutes. The solution was cooled to −20° C., a solution having 4.0 g (19 mmol) of 2,6-dichloro-4-trifluoromethylpyridine dissolved in 5 ml of tetrahydrofuran was added thereto, followed by stirring for 5 minutes, and a solution having 3.8 g (18 mmol) of 2,3,4-trimethoxy-6-methylbenzaldehyde dissolved in 7 ml of tetrahydrofuran was added thereto, followed by stirring for 1.5 hours. 30 ml of water was added to the mixture to terminate the reaction, and tetrahydrofuran was distilled off under reduced pressure. Extraction with ethyl acetate was carried out, the organic layer was dried over anhydrous sodium sulfate and subjected to filtration, and the solvent was distilled off under reduced pressure. The crude product thus obtained was purified by silica gel column chromatography to obtain 6.2 g (yield 81%) of (2,3,4-trimethoxy-6-methylphenyl)(2,6-dichloro-4-trifluoromethyl-3-pyridyl)methanol (brown oily substance).

(b) 14 g of manganese dioxide was added to a solution having 5.4 g of (2,3,4-trimethoxy-6-methylphenyl)(2,6-dichloro-4-trifluoromethyl-3-pyridyl)methanol obtained in step (a) dissolved in 140 ml of toluene, followed by stirring under reflux by heating for 6 hours. The mixture was cooled and then subjected to filtration, and toluene was distilled off under reduced pressure to obtain 4.4 g (yield 81%) of 3-(2,3,4-trimethoxy-6-methylbenzoyl)-2,6-dichloro-4-trifluoromethylpyridine (compound No. 3; m.p. 81–83° C.).

SYNTHESIS EXAMPLE 2
Synthesis of 3-(2,3,4-trimethoxy-6-methylbenzoyl)-2-chloro-4-trifluoromethylpyridine (compound No. 11) and 3-(2,3,4-trimethoxy-6-methylbenzoyl)-4-trifluoromethylpyridine (compound No. 7)

2.4 ml (17 mmol) of triethylamine and 0.3 g of 5% palladium carbon were added to a solution having 3.4 g (8.0 mmol) of 3-(2,3,4-trimethoxy-6-methylbenzoyl)-2,6-dichloro-4-trifluoromethylpyridine (compound No. 3) obtained in Synthesis Example 1 dissolved in 50 ml of methanol, followed by stirring under hydrogen atmosphere for 6.5 hours. The mixture was subjected to filtration, 50 ml of water was added thereto, and methanol was distilled off under reduced pressure. Extraction of ethyl acetate was carried out, the organic layer was dried over anhydrous sodium sulfate and subjected to filtration, and the solvent was distilled off under reduced pressure. The crude product thus obtained was purified by silica gel column chromatography to obtain 1.7 g (yield 55%) of 3-(2,3,4-trimethoxy-6-methylbenzoyl)-2-chloro-4-trifluoromethylpyridine (compound No. 11; m.p. 110–112° C.) and 1.1 g (yield 37%) of 3-(2,3,4-trimethoxy-6-methylbenzoyl)-4-trifluoromethylpyridine (compound No. 7; m.p. 59–62° C.).

SYNTHESIS EXAMPLE 3
Synthesis of 4-(2,3,4-trimethoxy-6-methylbenzoyl)-2,5-dichloro-3-trifluoromethylpyridine (compound No. 90)

(a) 17 ml (25 mmol) of n-butyllithium (1.5 M hexane solution) was dropwise added at 0° C. to a solution having 3.6 ml (25 mmol) of diisopropylamine dissolved in 60 ml of diethyl ether, followed by stirring for 45 minutes. The solution was cooled to −78° C., a solution having 6.0 g (24 mmol) of 2,3,6-trichloro-5-trifluoromethylpyridine dissolved in 8 ml of diethyl ether was added thereto, followed by stirring for 5 minutes, and a solution having 5.0 g (24 mmol) of 2,3,4-trimethoxy-6-methylbenzaldehyde dissolved in 12 ml of toluene was added thereto, followed by stirring for 1 hours. 30 ml of water was added to the mixture to terminate the reaction, the aqueous layer was extracted with ethyl acetate, and then the organic layer was dried over anhydrous sodium sulfate and subjected to filtration, and the solvent was distilled off under reduced pressure to obtain (2,3,4-trimethoxy-6-methylphenyl)(2,3,6-trichloro-5-trifluoromethyl-4-pyridyl)methanol (m.p. 131–135° C.).

(b) 2.7 ml (19 mmol) of triethylamine and 0.9 g of 5% palladium carbon were added to a solution having (2,3,4-trimethoxy-6-methylphenyl)(2,3,6-trichloro-5-trifluoromethyl-4-pyridyl)methanol obtained in step (a) dissolved in 200 ml of methanol, followed by stirring under hydrogen atmosphere for 14 hours. The mixture was subjected to filtration, 30 ml of water was added thereto, and methanol was distilled off under reduced pressure. Extraction with ethyl acetate was carried out, the organic layer was dried over anhydrous sodium sulfate and subjected to filtration, and the solvent was distilled off under reduced pressure. The crude product thus obtained was purified by silica gel column chromatography to obtain 2.38 g (yield 24%) of (2,3,4-trimethoxy-6-methylphenyl)(2,5-dichloro-3-trifluoromethyl-4-pyridyl)methanol (m.p. 162–165° C.).

(c) 14 g of manganese dioxide was added to a solution having 3.5 g (8.2 mmol) of (2,3,4-trimethoxy-6-methylphenyl)(2,915 5-dichloro-3-trifluoromethyl-4-pyridyl)methanol obtained in step (b) dissolved in 100 ml of toluene, followed by stirring under reflux by heating for 6 hours. The mixture was cooled and then subjected to filtration, and toluene was distilled off under reduced pressure. The crude product thus obtained was purified by silica gel column chromatography to obtain 3.1 g (yield 89%) of 4-(2,3,4-trimethoxy-6-methylbenzoyl-2,5-dichloro-3-trifluoromethylpyridine (compound No. 90; m.p. 106–109° C.).

SYNTHESIS EXAMPLE 4

Synthesis of 3-(4,5-dimethoxy-2-methylbenzoyl)-2-methoxy-4-trifluoromethylpyridine (compound No. 32)

0.9 g (16 mmol) of sodium methoxide was added to a solution having 1.5 g (4.2 mmol) of 3-(4,5-dimethoxy-2-methylbenzoyl)-2-chloro-4-trifluoromethylpyridine synthesized in accordance with a process in Synthesis Example 1 dissolved in 20 ml of toluene, followed by stirring under reflux by heating for 4 hours. The mixture was cooled, and then 20 ml of water was added thereto to terminate the reaction, the aqueous solution was extracted with ethyl acetate, and the organic layer was dried over anhydrous sodium sulfate and subjected to filtration by using a silica gel cake. The solvent was distilled off under reduced pressure to obtain 1.5 g (yield 99%) of 3-(4,5-dimethoxy-2-methylbenzoyl)-2-methoxy-4-trifluoromethylpyridine (compound No. 32; m.p. 125–127° C.).

SYNTHESIS EXAMPLE 5

Synthesis of 3-[4,5-(methylenedioxy)-2-methylbenzoyl]-2-chloro-4-trifluoromethylpyridine (compound No. 13)

(a) 3.2 ml (62 mmol) of bromine was dropwise added at 0° C. to a solution having 7.0 ml (58 mmol) of 3,4-(methylenedioxy)toluene and 5.5 ml (68 mmol) of pyridine dissolved in 110 ml of dichloromethane, followed by stirring for 30 minutes, and the temperature was raised to room temperature, followed by stirring for 22 hours. The mixture was washed with an aqueous sodium hydroxide solution, dried over anhydrous sodium sulfate and subjected to filtration, and the solvent was distilled off under reduced pressure. The crude product thus obtained was purified by silica gel column chromatography to obtain 13 g (yield 99%) of 2-bromo-4,5-(methylenedioxy)toluene.

(b) 13 ml (20 mmol) of n-butyllithium (1.5 M hexane solution) was dropwise added at –78° C. to a solution having 4.0 g (19 mmol) of 2-bromo-4,5-(methylenedioxy)toluene dissolved in 50 ml of tetrahydrofuran, followed by stirring for 30 minutes, and 1.5 ml (19 mmol) of dimethylformamide was added thereto, followed by stirring for 70 minutes. 30 ml of water was added to the mixture to terminate the reaction, and tetrahydrofuran was distilled off under reduced pressure. Extraction with chloroform was carried out, the organic layer was dried over anhydrous sodium sulfate and subjected to filtration by using a silica gel cake, and the solvent was distilled off under reduced pressure to obtain 3.1 g (yield 99%) of 2-methyl-4,5-(methylenedioxy)benzaldehyde (m.p. 84–86° C.).

(c) Using 1.5 g (8.3 mmol) of 2-chloro-4-trifluoromethylpyridine and 1.4 g (8.2 mmol) of 2-methyl-4,5-(methylenedioxy)benzaldehyde, 2.1 g (yield 73%) of (2-methyl-4,5-(methylenedioxy)phenyl)(2-chloro-4-trifluoromethyl-3-pyridyl)methanol (m.p. 127–130° C.) was obtained by a process in accordance with step (a) of Synthesis Example 1.

(d) Using 1.5 g (4.3 mmol) of (2-methyl-4,5-(methylenedioxy)phenyl)(2-chloro-4-trifluoromethyl-3-pyridyl)methanol obtained in step (c) and 8.0 g (92 mmol) of manganese dioxide, 0.3 g (yield 22%) of 3-[4,5-(methylenedioxy)-2-methylbenzoyl]-2-chloro-4-trifluoromethylpyridine (compound No. 13; m.p. 119–122° C.) was obtained by a process in accordance with step (b) of Synthesis Example 1.

SYNTHESIS EXAMPLE 6

Synthesis of 3-(5-benzyloxy-4-methoxy-2-methylbenzoyl)-2-chloro-4-trifluoromethylpyridine (compound No. 27)

(a) A dimethylformamide (15 ml) solution of 2-methoxy-4-methylphenol (6.91 g) was dropwise added to a dimethylformamide (20 ml) suspension of sodium hydride (2.4 g) under cooling with ice, followed by stirring for 30 minutes. A dimethylformamide (15 ml) solution of benzyl bromide (9.41 g) was dropwise added thereto, and tetrabutylammonium bromide in a catalytic amount was added thereto, followed by stirring at the same temperature for 30 minutes. The temperature was raised to room temperature and stirring was further carried out for one night. The reaction solution was poured into water (250 ml), and extraction with ethyl acetate (100 ml) was carried out three times. The ethyl acetate phase was washed with water (100 ml) three times and then washed with an aqueous sodium chloride solution (100 ml). After drying over magnesium sulfate, the solvent was distilled off under reduced pressure, the residue was purified by silica gel column chromatography (hexane-ethyl acetate) to obtain 11.4 g of 4-benzyloxy-3-methoxytoluene (m.p. 38–39° C.) quantitatively, and its structure was confirmed by nuclear magnetic resonance spectrum.

(b) 4-benzyloxy-3-methoxytoluene (8.0 g) was dissolved in dimethylformamide (30 ml and a dimethylformamide (15 ml) solution of N-bromosuccinimide (6.36 g) was dropwise added thereto, followed by stirring at room temperature for one night. The reaction solution was poured into ice water (400 ml), and crystals thus deposited were collected by filtration, adequately washed with water, and dried for one night to obtain 10.64 g of 4-benzyloxy-2-bromo-5-methoxytoluene (m.p. 110–111° C.) substantially quantitatively, and its structure was confirmed by nuclear magnetic resonance spectrum.

(c) A hexane solution (17 ml) of n-butyllithium was dropwise added to a tetrahydrofuran (190 ml) solution of 4-benzyloxy-2-bromo-5-methoxytoluene (7.83 g) at –78° C. over a period of 20 minutes, followed by stirring at the same temperature for 1 hour. A tetrahydrofuran (10 ml) solution of dimethylformamide (3.73 g) was dropwise added thereto at −78° C., followed by stirring at the same temperature for 1 hour. The temperature was gradually raised to room temperature, and stirring was further carried out for one night. The reaction solution was poured into an aqueous ammonium chloride solution (200 ml), and extraction with ethyl acetate (150 ml) was carried out twice. The ethyl acetate phase was washed with an aqueous sodium chloride solution (100 ml) twice and dried over magnesium sulfate, and the solvent was distilled off under reduced pressure. The residue was purified by silica gel column chromatography (hexane-ethyl acetate) to obtain 3.14 g (yield 48%) of 5-benzyloxy-4-methoxy-2-methylbenzaldehyde (m.p. 107–109° C.), and its structure was confirmed by nuclear magnetic resonance spectrum.

(d) A hexane solution (11.4 ml) of n-butyllithium was dropwise added to a tetrahydrofuran (45 ml) solution of diisopropylamine (2.81 g) at 0° C., followed by stirring for 1 hour to prepare a tetrahydrofuran solution of lithium diisopropylamide. The solution was cooled to −50° C., and a tetrahydrofuran (7.5 ml) solution of 2-chloro-4-trifluoromethylpyridine (2.81 g) was gradually added thereto, followed by stirring at the same temperature for 30 minutes. The solution was cooled to −78° C., and a tetrahydrofuran (37.5 ml) solution of 5-benzyloxy-4-methoxy-2-methylbenzaldehyde (3.97 g) was gradually added thereto, followed by stirring at the same temperature for 1 hour. A saturated aqueous ammonium chloride solution (50 ml) was added thereto, the temperature was raised to room temperature, the mixture was poured into a saturated aqueous sodium bicarbonate solution (50 ml), and extraction with ethyl acetate (150 ml) was carried out twice. The ethyl acetate phase was washed with an aqueous sodium chloride solution (100 ml) and dried over magnesium sulfate, and the solvent was distilled off under reduced pressure. The residue was purified by silica gel column chromatography (hexane-ethyl acetate) to obtain 6.48 g (yield 96%) of (5-benzyloxy-4-methoxy-2-methylphenyl)(2-chloro-4-trifluoromethyl-3-pyridyl)methanol as a red-yellow oily substance, and its structure was confirmed by nuclear magnetic resonance spectrum.

(e) (5-benzyloxy-4-methoxy-2-methylphenyl)(2-chloro-4-trifluoromethyl-3-pyridyl)methanol (5.9 g) was dissolved in a mixed solvent of anhydrous methylene chloride (50 ml) and acetonitrile (5 ml), and tetrapropylammonium perruthenate (95 ml), N-methylmorpholine-N-oxide (2.38 g) and molecular sieve 4A (6.8 g) were sequentially added thereto, followed by stirring in a stream of argon at room temperature for three nights. The reaction mixture was distilled off under reduced pressure, the residue thus obtained was suspended in methylene chloride and subjected to filtration by celite, and the residue was adequately washed with methylene chloride (200 ml). The solvent was distilled off under reduced pressure, and the residue was purified by silica gel column chromatography (hexane-ethyl acetate) to obtain 4.93 g (yield 84%) of 3-(5-benzyloxy-4-methoxy-2-methylbenzoyl)-2-chloro-4-trifluoromethylpyridine (compound No. 27; m.p. 116–117° C.), and its structure was confirmed by nuclear magnetic resonance spectrum.

SYNTHESIS EXAMPLE 7

Synthesis of 3-(2,3,4-trimethoxy-6-methylbenzoyl)-2-methylthio-4-trifluoromethylpyridine (compound No. 50)

Sodium methanethiolate (0.32 g) was added to a dimethylformamide (15 ml) solution of 0.9 g of 3-(2,3,4-trimethoxy-6-methylbenzoyl)-2-chloro-4-trifluoromethylpyridine (compound No. 11) at room temperature, followed by stirring for 1 hour. The mixture was poured into water (50 ml), and extraction with ethyl acetate was carried out. The ethyl acetate phase was dried over sodium sulfate, the solvent was distilled off under reduced pressure, and the residue was purified by silica gel column chromatography (hexane-ethyl acetate) to obtain 0.54 g (yield 58%) of 3-(2,3,4-trimethoxy-6-methylbenzoyl)-2-methylthio-4-trifluoromethylpyridine (compound No. 50; pale yellow oily substance), and its structure was confirmed by nuclear magnetic resonance spectrum.

SYNTHESIS EXAMPLE 8

Synthesis of 5-(2,3,4-trimethoxy-6-methylbenzoyl)-3-acetyl-2,6-dichloro-4-trifluoromethylpyridine (compound No. 62)

(a) 9.6 ml (14 mmol) of n-butyllithium (1.5 M hexane solution) was dropwise added to a tetrahydrofuran (16 ml) solution of 2.0 ml (14 mmol) of diisopropylamine at 0° C., followed by stirring for 30 minutes. The solution was cooled to −50° C., a tetrahydrofuran (11 ml) solution of 2.9 g (7 mmol) of (2,3,4-trimethoxy-6-methylphenyl)(2,6-dichloro-4-trifluoromethyl-3-pyridyl)methanol was added thereto, followed by stirring for 30 minutes, then the solution was cooled to −78° C., and acetaldehyde in an excess amount was added thereto, followed by stirring for 2 hours. 30 ml of water was added to the mixture to terminate the reaction, and tetrahydrofuran was distilled off under reduced pressure. Extraction with ethyl acetate was carried out, the organic layer was dried over anhydrous sodium sulfate and subjected to filtration, and the solvent was distilled off under reduced pressure. The crude product thus obtained was purified by silica gel column chromatography to obtain 2.5 g (yield 78%) of (2,3,4-trimethoxy-6-methylphenyl)(2,6-dichloro-5-(1-hydroxyethyl)-4-trifluoromethyl-3-pyridyl)methanol.

(b) 10 g of manganese dioxide was added to a toluene (80 ml) solution of 2.3 g (5 mmol) of (2,3,4-trimethoxy-6-methylphenyl)(2,6-dichloro-5-(1-hydroxyethyl)-4-trifluoromethyl-3-pyridyl)methanol obtained in step (a), followed by stirring under reflux by heating for 1 hour. The reaction solution was cooled to room temperature and then subjected to filtration, and toluene was distilled off under reduced pressure. The crude product thus obtained was purified by silica gel column chromatography to obtain 1.5 g (yield 66%) of 5-(2,3,4-trimethoxy-6-methylbenzoyl)-3-acetyl-2,6-dichloro-4-trifluoromethylpyridine (compound No. 62; m.p. 109–112° C.).

SYNTHESIS EXAMPLE 9

Synthesis of 4-(2,3,4-trimethoxy-6-methylbenzoyl)-2-chloro-3-trifluoromethyl-5-methoxypyridine (compound No. 123)

(a) 70.0 ml (106 mmol) of n-butyllithium (1.5 M hexane solution) was dropwise added to a diethyl ether 120 ml solution of 15.0 ml (107 mmol) of diisopropylamine at 0° C., followed by stirring for 1 hour. The solution was cooled to −78° C., a diethyl ether 10 ml solution of 22.1 g (102 mmol) of 2,3-dichloro-5-trifluoromethylpyridine was added thereto, followed by stirring for 30 minutes, and then a toluene 40 ml solution of 21.0 g (100 mmol) of 2,3,4-trimethoxy-6-methylbenzaldehyde was added thereto, followed by stirring for 2 hours. 30 ml of water was added to the mixture to terminate the reaction, the aqueous layer was extracted with ethyl acetate, and then the organic layer was dried over anhydrous sodium sulfate and subjected to filtration, and the solvent was distilled off under reduced pressure. The crude product thus obtained was purified by silica gel column chromatography to obtain 24.8 g (yield 58%) of (2,3,4-trimethoxy-6-methylphenyl)(2,3-dichloro-5-trifluoromethyl-4-pyridyl)methanol (m.p. 95–98° C.).

(b) 2.1 g of 5% palladium carbon was added to a methanol 200 ml solution of 24.8 g (58.1 mmol) of (2,3,4-trimethoxy-6-methylphenyl)(2,3-dichloro-5-trifluoromethyl-4-pyridyl)methanol obtained in step (a) and 9.50 ml (68.2 mmol) of triethylamine, followed by stirring under hydrogen atmosphere for 4 hours. The mixture was subjected to filtration, 50 ml of water was added thereto, and methanol was distilled off under reduced pressure. The aqueous layer was extracted with ethyl acetate, and the organic layer was dried over anhydrous sodium sulfate and subjected to filtration, and the solvent was distilled off under reduced pressure. The crude product thus obtained was purified by silica gel column chromatography to obtain 15.9 g (yield 70%) of (2,3,4-trimethoxy-6-methylphenyl)(3-chloro-5-trifluoromethyl-4-pyridyl)methanol (m.p. 102–105° C.).

(c) 45 g of manganese dioxide was added to a toluene 220 ml solution of 15.9 g (40.6 mmol) of (2,3,4-trimethoxy-6-methylphenyl)(3-chloro-5-trifluoromethyl-4-pyridyl)methanol obtained in step (b), followed by stirring under reflux by heating for 2 hours. The mixture was subjected to filtration, and the solvent was distilled off under reduced pressure to obtain 14.9 g (yield 94%) of 4-(2,3,4-trimethoxy-6-methylbenzoyl)-3-chloro-5-trifluoromethylpyridine (compound No. 102; m.p. 75–77° C.).

(d) 16.4 g (304 mmol) of sodium methoxide was added to a toluene 150 ml solution of 18.5 g (47.5 mmol) of 4-(2,3,4-trimethoxy-6-methylbenzoyl)-3-chloro-5-trifluoromethylpyridine obtained in step (c) and 16.6 ml (95.4 mmol) of hexamethylphosphoric triamide, followed by stirring under reflux by heating for 30 minutes. Water was added thereto to terminate the reaction, the aqueous layer was extracted with ethyl acetate, and the organic layer was dried over anhydrous sodium sulfate and subjected to filtration, and the solvent was distilled off under reduced pressure. The crude product thus obtained was purified by silica gel column chromatography to obtain 11.7 g (yield 64%) of 4-(2,3,4-trimethoxy-6-methylbenzoyl)-3-methoxy-5-trifluoromethylpyridine (compound No. 122; m.p. 103–106° C.).

(e) 6.1 g (28 mmol) of m-chloroperbenzoic acid (m-CPBA) was added to a chloroform 100 ml solution of 5.6 g (15 mmol) of 4-(2,3,4-trimethoxy-6-methylbenzoyl)-3-methoxy-5-trifluoromethylpyridine (compound No. 122) at 0° C., followed by stirring at room temperature for 18 hours. The reaction solution was washed with an aqueous sodium hydroxide solution, and the solvent was distilled off under reduced pressure to obtain 5.8 g (yield 99%) of 4-(2,3,4-trimethoxy-6-methylbenzoyl)-3-methoxy-5-trifluoromethylpyridine-N-oxide (m.p. 128–134° C.).

(f) 1.8 ml (19 mmol) of phosphorus oxychloride was added to 4 ml of toluene and 8 ml of dimethylformamide at 0° C., followed by stirring for 10 minutes, and 4.0 g (10 mmol) of 4-(2,3,4-trimethoxy-6-methylbenzoyl)-3-methoxy-5-trifluoromethylpyridine-N-oxide was added thereto, followed by stirring for 20 minutes. Stirring was carried out at room temperature for 2 hours, and then the reaction solution was poured into ice water to terminate the reaction. The aqueous layer was extracted with ethyl acetate, and then the organic layer was dried over anhydrous sodium sulfate and subjected to filtration, and the solvent was distilled off under reduced pressure. The crude product thus obtained was purified by silica gel column chromatography to obtain 3.57 g (yield 85%) of 4-(2,3,4-trimethoxy-6-methylbenzoyl)-2-chloro-3-trifluoromethyl-5-methoxypyridine (compound No. 123; m.p. 117–119° C.).

SYNTHESIS EXAMPLE 10

Synthesis of 4-(2,3,4-trimethoxy-6-methylbenzoyl)-2-bromo-3-trifluoromethyl-5-methoxypyridine (compound No. 124)

Using 7.2 g (18 mmol) of 4-(2,3,4-trimethoxy-6-methylbenzoyl)-3-methoxy-5-trifluoromethylpyridine-N-oxide, 7 ml of toluene, 17 ml of dimethylformamide and 10 g (35 mmol) of phosphorus oxybromide, 4.1 g (yield 49%) of 4-(2,3,4-trimethoxy-6-methylbenzoyl)-2-bromo-3-trifluoromethyl-5-methoxypyridine (compound No. 124; m.p. 145–147° C.) was obtained in the same process as in Synthesis Example 9 step (f).

SYNTHESIS EXAMPLE 11

Synthesis of 4-(2,3,4-trimethoxy-6-methylbenzoyl)-2,3,5-trichloropyridine (compound No. 186)

(a) 17.2 ml (26.7 mmol) of n-butyllithium (1.56 M hexane solution) was dropwise added to a diethyl ether (20 ml) solution of 2.7 g (26.7 mmol) of diisopropylamine at 0° C., followed by stirring for 1 hour. The solution was cooled to −78° C., a toluene solution of 4.8 g (26.7 mmol) of 2,3,5-trichloropyridine was dropwise added thereto, and then a toluene solution of 5.0 g (24.0 mmol) of 2,3,4-trimethoxy-6-methylbenzaldehyde was dropwise added thereto, followed by stirring for 30 minutes. The temperature was recovered to room temperature, and stirring was carried out further for 1 hour. 30 ml of water was added to the mixture to terminate the reaction, and ethyl acetate was added for extraction. The organic layer was dried over anhydrous sodium sulfate and subjected to filtration, and the solvent was distilled off under reduced pressure. The crude product thus obtained was purified by silica gel column chromatography to obtain 6.7 g (yield 72%) of amorphous (2,3,4-trimethoxy-6-methylphenyl)(2,3,5-trichloro-4-pyridyl)methanol.

(b) 16.2 g of manganese dioxide was added to a toluene (180 ml) solution of 5.6 g of (2,3,4-trimethoxy-6-methylphenyl)(2,3,5-trichloro-4-pyridyl)methanol obtained in step (a), followed by stirring under reflux by heating for 3 hours. After the mixture was cooled, it was subjected to filtration, and the solvent was distilled off under reduced pressure to obtain 4.7 g (yield 87%) of 4-(2,3,4-trimethoxy-6-methylbenzoyl)-2,3,5-trichloropyridine (compound No. 186; m.p. 60–61° C.).

SYNTHESIS EXAMPLE 12

Synthesis of 4-(2,3,4-trimethoxy-6-methylbenzoyl)-3,5-dichloropyridine (compound No. 191)

4.6 g (6.9 mmol) of triethylamine and 1.8 g of 10% palladium carbon were added to a methanol 280 ml solution of 17.8 g (4.6 mmol) of 4-(2,3,4-trimethoxy-6-methylbenzoyl)-2,3,5-trichloropyridine (compound No. 186), followed by stirring under hydrogen atmosphere at room temperature for 7 hours. The mixture was subjected to filtration, and the solvent was distilled off under reduced pressure. The crude product thus obtained was purified by silica gel column chromatography to obtain 11.6 g (yield 72%) of 4-(2,3,4-trimethoxy-6-methylbenzoyl)-3,5-dichloropyridine (compound No. 191; m.p. 109–111° C.).

SYNTHESIS EXAMPLE 13

Synthesis of 4-(2,3,4-trimethoxy-6-methylbenzoyl)-3-chloro-5-methoxypyridine (compound No. 244)

5.0 g (2.8 mmol) of hexamethylphosphoric triamide and 1.1 g (2.1 mmol) of sodium methoxide were added to a toluene (60 ml) solution of 5.0 g (1.4 mmol) of 4-(2,3,4-trimethoxy-6-methylbenzoyl)-3,5-dichloropyridine (compound No. 191), followed by stirring under reflux by heating for 5 hours. After the mixture was cooled, 50 ml of water was added to the mixture to terminate the reaction, and ethyl acetate was added thereto for extraction. The organic layer was dried over anhydrous sodium sulfate and subjected to filtration, and the solvent was distilled off under reduced pressure. The crude product thus obtained was purified by silica gel column chromatography to obtain 3.4 g (yield 69%) of 4-(2,3,4-trimethoxy-6-methylbenzoyl)-3-chloro-5-methoxypyridine (compound No. 244; pale yellow oily substance).

SYNTHESIS EXAMPLE 14

Synthesis of 4-(2,3,4-trimethoxy-6-methylbenzoyl)-2,3-dichloro-5-methoxypyridine (compound No. 193)

(a) A chloroform (60 ml) solution of 3.4 g (1 mmol) of 4-(2,3,4-trimethoxy-6-methylbenzoyl)-3-chloro-5-methoxypyridine (compound No. 244) was cooled with ice, 4.1 g (1.6 mmol) of m-chloroperbenzoic acid was added thereto, followed by stirring under cooling with ice for 2 hours, and stirring was further conducted at room temperature for 2 hours. 30 ml of a 0.5 mol/l aqueous sodium hydroxide solution was added to the mixture to terminate the reaction, the organic layer was dried over anhydrous sodium sulfate and subjected to filtration, and the solvent was distilled off under reduced pressure to obtain 3.5 g (yield 85%) of 4-(2,3,4-trimethoxy-6-methylbenzoyl)-3-chloro-5-methoxypyridine-N-oxide (m.p. 160–166° C.).

(b) 5 ml of dimethylformamide was added to 2.5 ml of toluene, the mixture was cooled with ice, and 1.3 ml (1.4 mmol) of phosphorus oxychloride was dropwise added thereto. After the mixture was stirred under cooling with ice for 10 minutes, 2.5 g (0.7 mmol) of 4-(2,3,4-trimethoxy-6-methylbenzoyl)-3-chloro-5-methoxypyridine-N-oxide was added thereto. After the mixture was stirred under cooling with ice for 30 minutes, the temperature was recovered to room temperature, followed by stirring for 2 hours. 30 ml of water was added to the mixture to terminate the reaction, and ethyl acetate was added thereto for extraction. The organic layer was dried over anhydrous sodium sulfate, subjected to filtration and purified by silica gel column chromatography to obtain 2.0 g (yield 76%) of 4-(2,3,4-trimethoxy-6-methylbenzoyl)-2,3-dichloro-5-methoxypyridine (compound No. 193; m.p. 98–99° C.).

SYNTHESIS EXAMPLE 15

Synthesis of 4-(2,3,4-trimethoxy-6-methylbenzoyl)-2bromo-3-chloro-5-methoxypyridine (compound No. 245)

5 ml of dimethylformamide was added to 2.5 ml of toluene, the mixture was cooled with ice, and 0.7 g (0.2 mmol) of phosphorus oxybromide was dropwise added thereto. After the mixture was stirred under cooling with ice for 10 minutes, 0.42 g (0.1 mmol) of 4-(2,3,4-trimethoxy-6-methylbenzoyl)-3-chloro-5-methoxypyridine-N-oxide obtained in Synthesis Example 14 (a) was added thereto. After the mixture was stirred under cooling with ice for 30 minutes, the temperature was recovered to room temperature, followed by stirring for 2 hours. 10 ml of water was added to the mixture to terminate the reaction, and ethyl acetate was added thereto for extraction. The organic layer was dried over anhydrous sodium sulfate, subjected to filtration and purified by silica gel column chromatography to obtain 0.32 g (yield 65%) of 4-(2,3,4-trimethoxy-6-methylbenzoyl)-2bromo-3-chloro-5-methoxypyridine (compound No. 245; m.p. 97–99° C.).

SYNTHESIS EXAMPLE 16

Synthesis of 4-(2,3,4-trimethoxy-6-methylbenzoyl)-3-bromo-5-methylpyridine (compound No. 228)

(a) 57.0 ml (88.9 mmol) of n-butyllithium (1.56 M hexane solution) was dropwise added to a diethyl ether (110 ml) solution of 12.5 ml (89.2 mmol) of diisopropylamine at 0° C., followed by stirring for 60 minutes. The solution was cooled to −78° C., a toluene (80 ml) solution of 20 g (85 mmol) of 3,5-dibromopyridine was added thereto, followed by stirring for 5 minutes, and then a toluene 50 ml solution of 21.0 g (100 mmol) of 2,3,4-trimethoxy-6-methylbenzaldehyde was added thereto, followed by stirring for 2 hours. 50 ml of water was added to the mixture to terminate the reaction, the aqueous layer was extracted with ethyl acetate, and the organic layer was dried over anhydrous sodium sulfate and subjected to filtration, and the solvent was distilled off under reduced pressure. The crude product thus obtained was purified by silica gel column chromatography to obtain 11.8 g (yield 31%) of (2,3,4-trimethoxy-6-methylphenyl)(3,5-dibromo-4-pyridyl)methanol (yellow oily substance).

(b) A tetrahydrofuran (15 ml) solution of 2.0 g (4.6 mmol) of (2,3,4-trimethoxy-6-methylphenyl)(3,5-dibromo-4-pyridyl)methanol obtained in step (a) was cooled to −78° C., 6.0 ml (9.4 mmol) of n-butyllithium (1.56 M hexane solution) was dropwise added thereto, followed by stirring for 5 minutes, and 0.5 ml (8.0 mmol) of methyl iodide was added thereto, followed by stirring for 2.5 hours. 20 ml of water was added, and tetrahydrofuran was distilled off under reduced pressure. The aqueous layer was extracted with ethyl acetate, the organic layer was dried over anhydrous sodium sulfate and subjected to filtration, and the solvent was distilled off under reduced pressure. The crude product thus obtained was purified by silica gel column chromatography to obtain 0.44 g (yield 25%) of (2,3,4-trimethoxy-6-methylphenyl)(3-bromo-5-methyl-4-pyridyl)methanol.

(c) 3 g of manganese dioxide was added to a toluene (30 ml) solution of 0.43 g (1.1 mmol) of (2,3,4-trimethoxy-6-methylphenyl)(3-bromo-5-methyl-4-pyridyl)methanol obtained in step (b), followed by stirring under reflux by heating for 2 hours. The mixture was subjected to filtration, the solvent was distilled off under reduced pressure, and the crude product thus obtained was purified by silica gel column chromatography to obtain 0.23 g (yield 54%) of 4-(2,3,4-trimethoxy-6-methylbenzoyl)-3-bromo-5-methylpyridine (compound No. 228; m.p. 88–93° C.).

Synthesis Example for an Intermediate

Now, Synthesis Example of 2,3,4-trimethoxy-6-methylbenzaldehyde to be used as an intermediate in the above Synthesis Examples 1, 3, 9, 11 and 16 is described below.

Synthesis of 2,3,4-trimethoxy-6-methylbenzaldehyde

A dry methylene chloride (100 ml) solution of 128 g (0.7 mol) of 3,4,5-trimethoxytoluene was dropwise added to a dry methylene chloride 500 ml solution of 112 g (0.84 mol) of aluminum chloride gradually under cooling with ice. The mixture was stirred at the same temperature for 45 minutes, a dry methylene chloride solution of 88.5 g (0.77 mol) of dichloromethyl methyl ether was dropwise added thereto gradually over a period of 2 hours. Stirring was conducted at the same temperature for 2 hours, and the mixture was gradually recovered to room temperature, followed by stirring at room temperature for one night. The reaction mixture was poured into 1 l of ice water, the methylene chloride phase was separated, and the aqueous phase was extracted with 200 ml of methylene chloride twice. The extract and the methylene chloride phase were combined together, sequentially washed with 200 ml of water, 200 ml of a saturated aqueous sodium bicarbonate solution and 200 ml of a saturated aqueous sodium chloride solution and dried over anhydrous magnesium sulfate, and the solvent was distilled off under reduced pressure. A seed for a crystal was inoculated into the residue, and the resulting crystal was collected by filtration, washed with hexane and air dried to obtain 128 g of 2,3,4-trimethoxy-6-methylbenzaldehyde (m.p. 55–57° C.).

Compounds produced by processes in accordance with Synthesis Examples 1 to 16 are shown in the following Tables 1 to 18.

Here, compounds represented by the formulae (I-1) to (I-9) in Tables are the following compounds. Further, in Tables, Me represents a methyl group, Et represents an ethyl group, Butyl represents a butyl group, i-Propyl represents an isopropyl group, Ph represents a phenyl group, Allyl represents an allyl group, c-Hexyl represents a cyclohexyl group, Benzyl represents a benzyl group, Propargyl represents a propargyl group, and Pentyl represents a pentyl group.

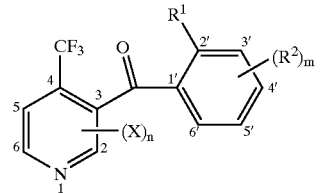
(I-1)

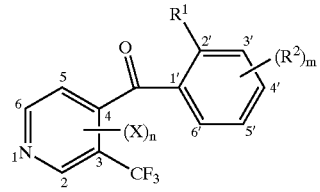
(I-2)

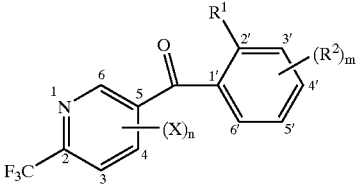
(I-3)

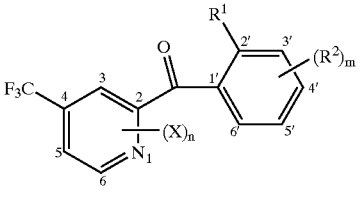
(I-4)

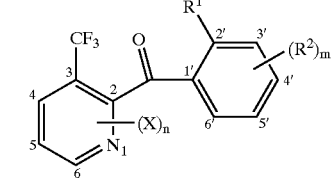
(I-5)

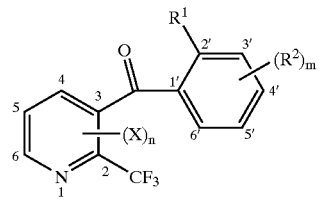
(I-6)

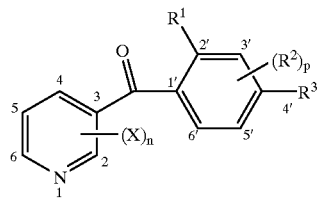
(I-7)

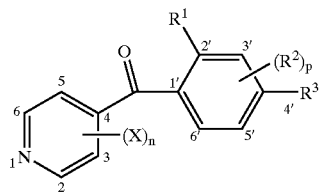
(I-8)

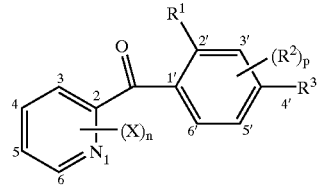
(I-9)

TABLE 1

Compounds represented by Formula (I-1)

| No. | $(X)_n$ | $R^1$ | $(R^2)_m$ | Physical properties |
|---|---|---|---|---|
| 1 | 2-Cl, 6-Cl | Me | 4'-MeO, 5'-MeO | m.p.108–110° C. |
| 2 | 2-Cl, 6-Cl | Me | 4'-MeO, 5'-Me | m.p.123–126° C. |
| 3 | 2-Cl, 6-Cl | Me | 4'-MeO, 5'-MeO, 6'-MeO | m.p.81–83° C. |
| 4 | 2-Cl, 6-Cl | Me | 4'-MeO | Colorless oily substance |
| 5 | Not substituted | Me | 4'-MeO, 5'-MeO | Yellow oily substance |
| 6 | Not substituted | Me | 4'-MeO, 5'-Me | m.p.63–65° C. |
| 7 | Not substituted | Me | 4'-MeO, 5'-MeO, 6'-MeO | m.p.59–62° C. |
| 8 | Not substituted | Me | 4'-MeO | Pale yellow oily substance |
| 9 | 2-Cl | Me | 4'-MeO, 5'-MeO | m.p.82–86° C. |
| 10 | 2-Cl | Me | 4'-MeO, 5'-Me | m.p.86–89° C. |
| 11 | 2-Cl | Me | 4'-MeO, 5'-MeO, 6'-MeO | m.p.110–112° C. |
| 12 | 2-Cl | Me | 4'-Me, 5'-Me, 6'-Me | m.p.88–95° C. |
| 13 | 2-Cl | Me | 4',5'-(—OCH$_2$O—) | m.p.119–122° C. |
| 14 | 2-Cl | Me | 4'-MeO | Pale yellow oily substance |
| 15 | 2-Cl | Et | 4'-MeO, 5'-MeO, 6'-MeO | |
| 16 | 2-Cl | i-Propyl | 4'-MeO, 5'-MeO, 6'-MeO | |
| 17 | 2-Cl | Me | 3'-MeO, 4'-MeO, 5'-MeO, 6'-MeO | |

TABLE 1-continued

Compounds represented by Formula (I-1)

| No. | (X)$_n$ | R$^1$ | (R$^2$)$_m$ | Physical properties |
|---|---|---|---|---|
| 18 | 2-Cl | Me | 4'-MeO, 5'-EtO | m.p.89–90° C. |
| 19 | 2-Cl | Me | 4'-MeO, 5'-i-Propyl—O— | Pale yellow oily substance |
| 20 | 2-Cl | Me | 4'-MeO, 5'-Allyl—O— | |
| 21 | 2-Cl | Me | 4'-MeO, 5'-Propargyl—O— | |
| 22 | 2-Cl | Me | 4'-MeO, 5'-CF$_3$CH$_2$O— | |
| 23 | 2-Cl | Me | 4'-MeO, 5'-c-Hexyl—O— | m.p.85–86° C. |

TABLE 2

Compounds represented by Formula (I-1)

| No. | (X)$_n$ | R$^1$ | (R$^2$)$_m$ | Physical properties |
|---|---|---|---|---|
| 24 | 2-Cl | Me | 4'-MeO, 5'-(CH$_3$)$_2$N(CH$_2$)$_2$O— | |
| 25 | 2-Cl | Me | 4'-MeO, 5'-CH$_3$S(CH$_2$)$_2$O— | |
| 26 | 2-Cl | Me | 4'-MeO, 5'-PhO— | |
| 27 | 2-Cl | Me | 4'-MeO, 5'-Benzyl—O— | m.p.116–117° C. |
| 28 | 2-Cl | Me | 4'-MeO, 5'-CH$_3$COO— | |
| 29 | 2-Cl | Me | 4'-MeO, 5'-CH$_3$OCOO— | |
| 30 | 2-MeO, 6-MeO | Me | 4'-MeO, 5'-MeO, 6'-MeO | m.p.93–94° C. |
| 31 | 2-Cl, 6-MeO | Me | 4'-MeO, 5'-MeO, 6'-MeO | m.p.85–87° C. |
| 32 | 2-MeO | Me | 4'-MeO, 5'-MeO | m.p.125–127° C. |
| 33 | 2-i-Propyl—O— | Me | 4'-MeO, 5'-MeO, 6'-MeO | Pale yellow oily substance |
| 34 | 2-CF$_3$CH$_2$O— | Me | 4'-MeO, 5'-MeO, 6'-MeO | m.p.80–82° C. |
| 35 | 2-CH$_3$O(CH$_2$)$_2$O— | Me | 4'-MeO, 5'-MeO, 6'-MeO | Pale yellow oily substance |
| 36 | 2-CH$_3$S(CH$_2$)$_2$O— | Me | 4'-MeO, 5'-MeO, 6'-MeO | Pale yellow oily substance |
| 37 | 2-PhO— | Me | 4'-MeO, 5'-MeO, 6'-MeO | Pale yellow oily substance |
| 38 | 2-Benzyl—O— | Me | 4'-MeO, 5'-MeO, 6'-MeO | Pale yellow oily substance |
| 39 | 2-c-Hexyl—O— | Me | 4'-MeO, 5'-MeO, 6'-MeO | Pale yellow oily substance |
| 40 | 2-Allyl—O— | Me | 4'-MeO, 5'-MeO, 6'-MeO | m.p.85–86° C. |
| 41 | 2-Propargyl—O— | Me | 4'-MeO, 5'-MeO, 6'-MeO | m.p.121–124° C. |
| 42 | 2-(CH$_3$)$_2$N(CH$_2$)$_2$O— | Me | 4'-MeO, 5'-MeO, 6'-MeO | Pale yellow oily substance |
| 43 | 2-Cl, 5-Me | Me | 4'-MeO, 5'-MeO, 6'-MeO | m.p.161–162° C. |
| 44 | 2-Cl, 5-Allyl | Me | 4'-MeO, 5'-MeO, 6'-MeO | |

TABLE 2-continued

Compounds represented by Formula (I-1)

| No. | (X)$_n$ | R$^1$ | (R$^2$)$_m$ | Physical properties |
|---|---|---|---|---|
| 45 | 2-Cl, 5-Propargyl | Me | 4'-MeO, 5'-MeO, 6'-MeO | |
| 46 | 2-Cl, 5-CH$_3$O(C=O)— | Me | 4'-MeO, 5'-MeO, 6'-MeO | |
| 47 | 2-Cl, 5-CH$_3$(C=O)— | Me | 4'-MeO, 5'-MeO, 6'-MeO | m.p.127–129° C. |

TABLE 3

Compounds represented by Formula (I-1)

| No. | (X)$_n$ | R$^1$ | (R$^2$)$_m$ | Physical properties |
|---|---|---|---|---|
| 48 | 2-Cl, 5-Et | Me | 4'-MeO, 5'-MeO, 6'-MeO | |
| 49 | 2-MeO, 5-Me | Me | 4'-MeO, 5'-MeO, 6'-MeO | |
| 50 | 2-MeS | Me | 4'-MeO, 5'-MeO, 6'-MeO | Pale yellow oily substance |
| 51 | 2-Me$_2$N | Me | 4'-MeO, 5'-MeO, 6'-MeO | Pale yellow oily substance |
| 52 | 2-Cl, 5-(CH$_3$)$_2$N(C=O)— | Me | 4'-MeO, 5'-MeO, 6'-MeO | |
| 53 | 2-CN | Me | 4'-MeO, 5'-MeO, 6'-MeO | m.p. 140–144° C. |
| 54 | 2-Cl, 5-Cl, 6-Cl | Me | 4'-MeO, 5'-MeO, 6'-MeO | m.p. 114–116° C. |
| 55 | 2-Cl, 5-Cl | Me | 4 MeO, 5'-MeO, 6'-MeO | m.p. 149–151° C. |
| 56 | 2-MeO, 5-Cl | Me | 4'-MeO, 5'-MeO, 6'-MeO | m.p. 100–103° C. |
| 57 | 2-OH, 5-Cl | Me | 4'-MeO, 5'-MeO, 6'-MeO | |
| 58 | 2-Cl, 5-Me, 6-Cl | Me | 4'-MeO, 5'-MeO, 6'-MeO | m.p. 101–104° C. |
| 59 | 2-Cl, 5-Allyl, 6-Cl | Me | 4'-MeO, 5'-MeO, 6'-MeO | Pale yellow oily substance |
| 60 | 2-Cl, 5-Propargyl, 6-Cl | Me | 4'-MeO, 5'-MeO, 6'-MeO | |
| 61 | 2-Cl, 5-CH$_3$O(C=O)—, 6-Cl | Me | 4'-MeO, 5'-MeO, 6'-MeO | m.p. 107–111° C. |
| 62 | 2-Cl, 5-CH$_3$(C=O)—, 6-Cl | Me | 4'-MeO, 5'-MeO, 6'-MeO | m.p. 109–112° C. |
| 63 | 2-Cl, 5-Et, 6-Cl | Me | 4'-MeO, 5'-MeO, 6'-MeO | |
| 64 | 2-Cl, 5-(CH$_3$)$_2$N(C=O)— | Me | 4'-MeO, 5'-MeO, 6'-MeO | |
| 65 | 5-Me | Me | 4'-MeO, 5'-MeO, 6'-MeO | Pale yellow oily substance |
| 66 | 5-Allyl | Me | 4'-MeO, 5'-MeO, 6'-MeO | |
| 67 | 5-Propargyl | Me | 4'-MeO, 5'-MeO, 6'-MeO | |
| 68 | 5-CH$_3$O(C=O)— | Me | 4'-MeO, 5'-MeO, 6'-MeO | |
| 69 | 5-CH$_3$(C=O)— | Me | 4'-MeO, 5'-MeO, 6'-MeO | m.p. 110–113° C. |
| 70 | 5-Et | Me | 4'-MeO, 5'-MeO, 6'-MeO | |

TABLE 4

Compounds represented by Formula (I-1)

| No. | (X)$_n$ | R$^1$ | (R$^2$)$_m$ | Physical properties |
|---|---|---|---|---|
| 71 | 5-(CH$_3$)$_2$N(C=O)— | Me | 4'-MeO, 5'-MeO, 6'-MeO | |
| 72 | 2-CH$_3$O(CH$_2$)$_2$O— | Me | 4'-MeO, 5'-MeO, 6'-MeO | m.p. 77–81° C. |
| 73 | 2-(6'-phenyl)—O— | Me | 4'-MeO, 5'-MeO, 6'-O-(2-Pyridyl) | m.p. 183–189° C. |
| 74 | 2-MeO | Me | 4'-MeO, 5'-MeO, 6'-MeO | m.p. 81–82° C. |
| 75 | 2-EtO | Me | 4'-MeO, 5'-MeO, 6'-MeO | Pale yellow oily substance |
| 76 | 2-MeS | Me | 4'-MeO, 5'-MeO, 6'-OH | m.p. 98–102° C. |
| 77 | 2-OH | Me | 4'-MeO, 5'-MeO, 6'-MeO | m.p. 167–173° C. |
| 78 | 2-NH$_2$ | Me | 4'-MeO, 5'-MeO, 6'-MeO | m.p. 115–118° C. |
| 79 | 2-CH$_3$NH | Me | 4'-MeO, 5'-MeO, 6'-MeO | m.p. 150–157° C. |
| 80 | 2-CH$_3$COO | Me | 4'-MeO, 5'-MeO, 6'-MeO | Pale yellow oily substance |
| 81 | 2-i-Propyl—O | Me | 4'-MeO, 5'-MeO, 6'-i-Propyl—O | Pale yellow oily substance |
| 82 | 2-Cl, 6-Cl | Et | 4'-MeO, 5'-MeO, 6'-MeO | m.p. 105–108° C. |
| 83 | 2-Cl | Me | 4'-MeO, 5'-(4-MeO—Benzyl)O | m.p. 123–125° C. |
| 84 | 2-Me | Me | 4'-MeO, 5'-MeO, 6'-MeO | m.p. 100–103° C. |
| 85 | 2-Me, 5-Cl | Me | 4'-MeO, 5'-MeO, 6'-MeO | |
| 86 | 2-Me, 5-Br | Me | 4'-MeO, 5'-MeO, 6'-MeO | |

TABLE 5

Compounds represented by Formula (I-2)

| No. | (X)$_n$ | R$^1$ | (R$^2$)$_m$ | Physical properties |
|---|---|---|---|---|
| 87 | 2-PhO, 5-Cl | Me | 4'-MeO, 5'-MeO, 6'-MeO | m.p. 147–150° C. |
| 88 | 2-OH, 5-Cl | Me | 4'-MeO, 5'-MeO, 6'-MeO | |

TABLE 6

Compounds represented by Formula (I-2)

| No. | (X)$_n$ | R$^1$ | (R$^2$)$_m$ | Physical properties |
|---|---|---|---|---|
| 89 | 2-Cl, 5-Cl | Me | 4'-MeO, 5'-MeO | m.p.120–125° C. |
| 90 | 2-Cl, 5-Cl | Me | 4'-MeO, 5'-MeO, 6'-MeO | m.p.106–109° C. |
| 91 | Not substituted | Me | 4'-MeO, 5'-MeO | m.p.98–101° C. |
| 92 | Not substituted | Me | 4'-MeO, 5'-MeO, 6'-MeO | m.p.104–107° C. |
| 93 | 2-MeO, 5-Cl | Me | 4'-MeO, 5'-MeO, 6'-MeO | m.p.130–134° C. |
| 94 | 2-MeO 5-Cl | Me | 4'-MeO, 5'-MeO, 6'-MeO | m.p.151–156° C. |
| 95 | 2-Br, 5-Cl | Me | 4'-MeO, 5'-MeO, 6'-MeO | |
| 96 | 2-MeS, 5-Cl | Me | 4'-MeO, 5'-MeO, 6'-MeO | |
| 97 | 2-CN, 5-Cl | Me | 4'-MeO, 5'-MeO, 6'-MeO | |
| 98 | 2-Cl, 5-Cl, 6-Cl | Me | 4'-MeO, 5'-MeO | m.p.139–141° C. |
| 99 | 2-Cl, 5-Cl, 6-Cl | Me | 4'-MeO, 5'-MeO, 6'-MeO | m.p.113–115° C. |
| 100 | 5-Cl, 6-Cl | Me | 4'-MeO, 5'-MeO | m.p.94–97° C. |
| 101 | 5-Cl | Me | 4'-MeO, 5'-MeO | m.p.90–91° C. |
| 102 | 5-Cl | Me | 4'-MeO, 5'-MeO, 6'-MeO | m.p.75–77° C. |
| 103 | 5-Cl, 6-Cl | Me | 4'-MeO, 5'-MeO, 6'-MeO | m.p.72–74° C. |
| 104 | 5-Cl, 6-MeO | Me | 4'-MeO, 5'-MeO, 6'-MeO | m.p.143–146° C. |
| 105 | 5-Cl, 6-MeO | Me | 4'-MeO, 5'-MeO | m.p.112–115° C. |
| 106 | 5-Cl, 6-EtO | Me | 4'-MeO, 5'-MeO, 6'-MeO | m.p.82–84° C. |
| 107 | 6-MeO | Me | 4'-MeO, 5'-MeO, 6'-MeO | Pale yellow oily substance |
| 108 | 5-Cl, 6-n-Propyl—O | Me | 4'-MeO, 5'-MeO, 6'-MeO | Pale yellow oily substance |
| 109 | 6-EtO | Me | 4'-MeO, 5'-MeO, 6'-MeO | Pale yellow oily substance |
| 110 | 5-Cl, 6-n-Butyl—O | Me | 4'-MeO, 5'-MeO, 6'-MeO | Pale yellow oily substance |
| 111 | 6-n-Propyl—O | Me | 4'-MeO, 5'-MeO, 6'-MeO | Pale yellow oily substance |
| 112 | 6-n-Butyl—O | Me | 4'-MeO, 5'-MeO, 6'-MeO | Pale yellow oily substance |

TABLE 7

Compounds represented by Formula (I-2)

| No. | (X)$_n$ | R$^1$ | (R$^2$)$_m$ | Physical properties |
|---|---|---|---|---|
| 113 | 5-Cl, 6-Propargyl—O | Me | 4'-MeO, 5'-MeO, 6'-MeO | m.p.131–133° C. |
| 114 | 5-Cl, 6-n-Pentyl—O | Me | 4'-MeO, 5'-MeO, 6'-MeO | Pale yellow oily substance |
| 115 | 5-Cl, 6-OH | Me | 4'-MeO, 5'-MeO, 6'-MeO | 152–154° C. |
| 116 | 6-n-Pentyl—O | Me | 4'-MeO, 5'-MeO, 6'-MeO | Pale yellow oily substance |
| 117 | 5-Cl, 6-CH$_3$S(CH$_2$)$_2$O | Me | 4'-MeO, 5'-MeO, 6'-MeO | m.p.62–64° C. |
| 118 | 5-Cl, 6-Allyl—O | Me | 4'-MeO, 5'-MeO, 6'-MeO | Pale yellow oily substance |
| 119 | 5-Cl, 6-CH$_3$O(CH$_2$)$_2$O | Me | 4'-MeO, 5'-MeO, 6'-MeO | m.p.78–80° C. |
| 120 | 2-MeO, 5-MeO | Me | 4'-MeO, 5'-MeO, 6'-MeO | m.p.135–139° C. |
| 121 | 2-MeO | Me | 4'-MeO, 5'-MeO, 6'-MeO | m.p.97–100° C. |
| 122 | 5-MeO | Me | 4'-MeO, 5'-MeO, 6'-MeO | m.p.103–106° C. |
| 123 | 2-Cl, 5-MeO | Me | 4'-MeO, 5'-MeO, 6'-MeO | m.p.117–119° C. |
| 124 | 2-Br, 5-MeO | Me | 4'-MeO, 5'-MeO, 6'-MeO | m.p.145–147° C. |
| 125 | 2-Me, 5-MeO | Me | 4'-MeO, 5'-MeO, 6'-MeO | |
| 126 | 2-Et, 5-MeO | Me | 4'-MeO, 5'-MeO, 6'-MeO | |
| 127 | 2-n-Propyl, 5-MeO | Me | 4'-MeO, 5'-MeO, 6'-MeO | |
| 128 | 2-Allyl, 5-MeO | Me | 4'-MeO, 5'-MeO, 6'-MeO | |
| 129 | 2-Propargyl, 5-MeO | Me | 4'-MeO, 5'-MeO, 6'-MeO | |

TABLE 7-continued

Compounds represented by Formula (I-2)

| No. | (X)$_n$ | R$^1$ | (R$^2$)$_m$ | Physical properties |
|---|---|---|---|---|
| 130 | 2-EtO, 5-MeO | Me | 4'-MeO, 5'-MeO, 6'-MeO | m.p.110–112° C. |
| 131 | 2-CN, 5-MeO | Me | 4'-MeO, 5'-MeO, 6'-MeO | m.p.117–120° C. |
| 132 | 2-MeS, 5-MeO | Me | 4'-MeO, 5'-MeO, 6'-MeO | m.p.154–159° C. |
| 133 | 5-Me | Me | 4'-MeO, 5'-MeO, 6'-MeO | m.p.98–105° C. |
| 134 | 5-Br | Me | 4'-MeO, 5'-MeO, 6'-MeO | |
| 135 | 5-F | Me | 4'-MeO, 5'-MeO, 6'-MeO | |

TABLE 8

Compound represented by Formula (I-3)

| No. | (X)$_n$ | R$^1$ | (R$^2$)$_m$ | Physical properties |
|---|---|---|---|---|
| 136 | 6-Cl | Me | 4'-MeO, 5'-MeO, 6'-MeO | Yellow oily substance |

TABLE 9

Compound represented by Formula (I-4)

| No. | (X)$_n$ | R$^1$ | (R$^2$)$_m$ | Physical properties |
|---|---|---|---|---|
| 137 | Not substituted | Me | 4'-MeO, 5'-MeO, 6'-MeO | |

TABLE 10

Compound represented by Formula (I-5)

| No. | (X)$_n$ | R$^1$ | (R$^2$)$_m$ | Physical properties |
|---|---|---|---|---|
| 138 | 5-Cl, 6-Cl | Me | 4'-MeO, 5'-MeO, 6'-MeO | m.p. 109–111° C. |

TABLE 11

Compounds represented by Formula (I-6)

| No. | (X)$_n$ | R$^1$ | (R$^2$)$_m$ | Physical properties |
|---|---|---|---|---|
| 139 | 4-Me | Me | 4'-MeO, 5'-MeO, 6'-MeO | |
| 140 | 4-Me, 5-Cl | Me | 4'-MeO, 5'-MeO, 6'-MeO | |
| 141 | 4-Me, 5-Br | Me | 4'-MeO, 5'-MeO, 6'-MeO | |

TABLE 12

| No. | Formula | (X)$_n$ | R$^1$ | (R$^2$)$_p$ | R$^3$ | Physical properties |
|---|---|---|---|---|---|---|
| 142 | (I-7) | 2-MeO | Me | 5'-MeO | MeO | m.p. 90–91° C. |
| 143 | (I-7) | 2-Cl, 4-Cl | Me | 5'-MeO | PhO | |
| 144 | (I-7) | 2-Cl, 4-Cl | Me | 5'-MeO, 6'-MeO | MeO | |
| 145 | (I-7) | 2-Cl, 4-MeO | Me | 5'-MeO, 6'-MeO | MeO | |
| 146 | (I-7) | 2-MeO, 4-Cl | Me | 5'-MeO, 6'-MeO | MeO | |
| 147 | (I-7) | 2-F, 4-F | Me | 5'-MeO, 6'-MeO | MeO | |
| 148 | (I-7) | 2-F, 4-MeO | Me | 5'-MeO, 6'-MeO | MeO | |
| 149 | (I-7) | 2-MeO, 4-F | Me | 5'-MeO, 6'-MeO | MeO | |
| 150 | (I-7) | 2-Cl, 4-Cl, 5-Cl | Me | 5'-MeO, 6'-MeO | MeO | |
| 151 | (I-7) | 2-Me, 4-Me | Me | 5'-MeO, 6'-MeO | MeO | |
| 152 | (I-7) | 2-Me, 4-Me, 5-Cl | Me | 5'-MeO, 6'-MeO | MeO | |
| 153 | (I-7) | 2-Me, 4-Me, 5-Br | Me | 5'-MeO, 6'-MeO | MeO | |
| 154 | (I-7) | 2-Me, 4-MeO | Me | 5'-MeO, 6'-MeO | MeO | |
| 155 | (I-7) | 2-Me, 4-MeO, 5-Cl | Me | 5'-MeO, 6'-MeO | MeO | |
| 156 | (I-7) | 2-Me, 4-MeO, 5-Br | Me | 5'-MeO, 6'-MeO | MeO | |
| 157 | (I-7) | 2-MeO, 4-Me | Me | 5'-MeO, 6'-MeO | MeO | |
| 158 | (I-7) | 2-MeO, 4-Me, 5-Cl | Me | 5'-MeO, 6'-MeO | MeO | |
| 159 | (I-7) | 2-MeO, 4-Me, 5-Br | Me | 5'-MeO, 6'-MeO | MeO | |
| 160 | (I-7) | 2-Me, 4-Cl | Me | 5'-MeO, 6'-MeO | MeO | |
| 161 | (I-7) | 2-Me, 4-Cl, 5-Cl | Me | 5'-MeO, 6'-MeO | MeO | |
| 162 | (I-7) | 2-Me, 4-Cl, 5-Br | Me | 5'-MeO, 6'-MeO | MeO | |
| 163 | (I-7) | 2-Cl, 4-Me | Me | 5'-MeO, 6'-MeO | MeO | |
| 164 | (I-7) | 2-Cl, 4-Me, 5-Cl | Me | 5'-MeO, 6'-MeO | MeO | |
| 165 | (I-7) | 2-Cl, 4-Me, 5-Br | Me | 5'-MeO, 6'-MeO | MeO | |
| 166 | (I-7) | 2-CF$_3$, 4-CF$_3$, 6-Cl | Me | 5'-MeO, 6'-MeO | MeO | |

TABLE 13

| No. | Formula | $(X)_n$ | $R^1$ | $(R^2)_p$ | $R^3$ | Physical properties |
|---|---|---|---|---|---|---|
| 167 | (I-7) | 2-Cl, 4-CF$_3$, 6-CF$_3$ | Me | 5'-MeO, 6'-MeO | MeO | m.p. 117–118° C. |
| 168 | (I-7) | 2-CF$_3$, 4-CF$_3$, 5-Me | Me | 5'-MeO, 6'-MeO | MeO | |
| 169 | (I-7) | 2-CF$_3$, 4-CF$_3$, 5-Et | Me | 5'-MeO, 6'-MeO | MeO | |
| 170 | (I-7) | 2-CF$_3$, 4-CF$_3$, 5-Allyl | Me | 5'-MeO, 6'-MeO | MeO | |
| 171 | (I-7) | 2-CF$_3$, 4-CF$_3$, 5-n-Propyl | Me | 5'-MeO, 6'-MeO | MeO | |
| 172 | (I-7) | 2-CF$_3$, 4-CF$_3$, 5-Propargyl | Me | 5'-MeO, 6'-MeO | MeO | |
| 173 | (I-7) | 2-CF$_3$, 4-CF$_3$, 5-Me, 6-Cl | Me | 5'-MeO, 6'-MeO | MeO | |
| 174 | (I-7) | 2-CF$_3$, 4-CF$_3$, 5-Et, 6-Cl | Me | 5'-MeO, 6'-MeO | MeO | |
| 175 | (I-7) | 2-CF$_3$, 4-CF$_3$, 5-Allyl, 6-Cl | Me | 5'-MeO, 6'-MeO | MeO | |
| 176 | (I-7) | 2-CF$_3$, 4-CF$_3$, 5-n-Propyl, 6-Cl | Me | 5'-MeO, 6'-MeO | MeO | |
| 177 | (I-7) | 2-CF$_3$, 4-CF$_3$, 5-Propargyl, 6-Cl | Me | 5'-MeO, 6'-MeO | MeO | |
| 178 | (I-7) | 2-CF$_3$, 4-CF$_3$ | Me | 5'-MeO, 6'-MeO | MeO | |
| 179 | (I-7) | 2-CF$_3$, 5-CF$_3$, 6-Cl | Me | 5'-MeO, 6'-MeO | MeO | |
| 180 | (I-7) | 2-CF$_3$, 5-CF$_3$ | Me | 5'-MeO, 6'-MeO | MeO | |
| 181 | (I-7) | 2-CF$_3$, 4-Me, 5-CF$_3$ | Me | 5'-MeO, 6'-MeO | MeO | |
| 182 | (I-7) | 2-CF$_3$, 4-Et, 5-CF$_3$ | Me | 5'-MeO, 6'-MeO | MeO | |
| 183 | (I-7) | 2-CF$_3$, 4-Allyl, 5-CF$_3$ | Me | 5'-MeO, 6'-MeO | MeO | |
| 184 | (I-7) | 2-CF$_3$, 4-n-propyl, 5-CF$_3$ | Me | 5'-MeO, 6'-MeO | MeO | |
| 185 | (I-7) | 2-CF$_3$, 4-propargyl, 5-CF$_3$ | Me | 5'-MeO, 6'-MeO | MeO | |
| 186 | (I-8) | 2-Cl, 3-Cl, 5-Cl | Me | 5'-MeO, 6'-MeO | MeO | m.p. 60–61° C. |
| 187 | (I-8) | 2-MeO, 3-Cl, 5-Cl | Me | 5'-MeO, 6'-MeO | MeO | m.p. 128–134° C. |

TABLE 14

| No. | Formula | $(X)_n$ | $R^1$ | $(R^2)_p$ | $R^3$ | Physical properties |
|---|---|---|---|---|---|---|
| 188 | (I-8) | 2-EtO, 3-Cl, 5-Cl | Me | 5'-MeO, 6'-MeO | MeO | Pale yellow oily substance |
| 189 | (I-8) | 2-MeO, 3-MeO, 5-Cl | Me | 5'-MeO, 6'-MeO | MeO | Pale yellow oily substance |
| 190 | (I-8) | 2-MeO, 3-MeO | Me | 5'-MeO, 6'-MeO | MeO | Pale yellow oily substance |
| 191 | (I-8) | 3-Cl, 5-Cl | Me | 5'-MeO, 6'-MeO | MeO | m.p. 190–111° C. |
| 192 | (I-8) | 3-Cl | Me | 5'-MeO, 6'-MeO | MeO | m.p. 90–94° C. |
| 193 | (I-8) | 2-Cl, 3-Cl, 5-MeO | Me | 5'-MeO, 6'-MeO | MeO | m.p. 98–99° C. |
| 194 | (I-8) | 2-Cl, 3-Cl, 5-EtO | Me | 5'-MeO, 6'-MeO | MeO | m.p. 110–114° C. |
| 195 | (I-8) | 2-Cl, 3-MeO, 5-MeO | Me | 5'-MeO, 6'-MeO | MeO | |
| 196 | (I-8) | 2-Cl, 3-EtO, 5-MeO | Me | 5'-MeO, 6'-MeO | MeO | |
| 197 | (I-8) | 3-MeO | Me | 5'-MeO, 6'-MeO | MeO | |
| 198 | (I-8) | 3-EtO | Me | 5'-MeO, 6'-MeO | MeO | |
| 199 | (I-8) | 2-Cl, 3-MeO, 5-Cl | Me | 5'-MeO, 6'-MeO | MeO | m.p. 80–86° C. |
| 200 | (I-8) | 2-Cl, 3-EtO, 5-Cl | Me | 5'-MeO, 6'-MeO | MeO | Pale yellow oily substance |
| 201 | (I-8) | 3-Br | Me | 5'-MeO, 6'-MeO | MeO | m.p. 106–107° C. |
| 202 | (I-8) | 3-Br, 5-Br | Me | 5'-MeO, 6'-MeO | MeO | m.p. 108–110° C. |
| 203 | (I-8) | 3-Br, 5-MeO | Me | 5'-MeO, 6'-MeO | MeO | Pale yellow oily substance |
| 204 | (I-8) | 2-F, 3-F, 5-F | Me | 5'-MeO, 6'-MeO | MeO | |
| 205 | (I-8) | 2-MeO, 3-F, 5-F | Me | 5'-MeO, 6'-MeO | MeO | |
| 206 | (I-8) | 2-EtO, 3-F, 5-F | Me | 5'-MeO, 6'-MeO | MeO | |
| 207 | (I-8) | 2-MeO, 3-MeO, 5-F | Me | 5'-MeO, 6'-MeO | MeO | |
| 208 | (I-8) | 3-F, 5-F | Me | 5'-MeO, 6'-MeO | MeO | |
| 209 | (I-8) | 3-F | Me | 5'-MeO, 6'-MeO | MeO | |
| 210 | (I-8) | 3-Me, 5-MeO | Me | 5'-MeO, 6'-MeO | MeO | Pale yellow oily substance |

TABLE 15

| No. | Formula | (X)$_n$ | R$^1$ | (R$^2$)$_p$ | R$^3$ | Physical properties |
|---|---|---|---|---|---|---|
| 211 | (I-8) | 2-Cl, 3-Me, 5-MeO | Me | 5'-MeO, 6'-MeO | MeO | Pale yellow oily substance |
| 212 | (I-8) | 2-Br, 3-Me, 5-MeO | Me | 5'-MeO, 6'-MeO | MeO | |
| 213 | (I-8) | 3-Me, 5-Me | Me | 5'-MeO, 6'-MeO | MeO | m.p. 117–122° C. |
| 214 | (I-8) | 2-Cl, 3-Me, 5-Me | Me | 5'-MeO, 6'-MeO | MeO | |
| 215 | (I-8) | 2-Br, 3-Me, 5-Me | Me | 5'-MeO, 6'-MeO | MeO | |
| 216 | (I-8) | 3-Et, 5-MeO | Me | 5'-MeO, 6'-MeO | MeO | |
| 217 | (I-8) | 3-Allyl, 5-MeO | Me | 5'-MeO, 6'-MeO | MeO | |
| 218 | (I-8) | 3-n-Propyl, 5-MeO | Me | 5'-MeO, 6'-MeO | MeO | |
| 219 | (I-8) | 3-Propargyl, 5-MeO | Me | 5'-MeO, 6'-MeO | MeO | |
| 220 | (I-8) | 2-Cl, 3-Et, 5-MeO | Me | 5'-MeO, 6'-MeO | MeO | |
| 221 | (I-8) | 2-Cl, 3-Allyl, 5-MeO | Me | 5'-MeO, 6'-MeO | MeO | |
| 222 | (I-8) | 2-Cl, 3-n-Propyl, 5-MeO | Me | 5'-MeO, 6'-MeO | MeO | |
| 223 | (I-8) | 2-Cl, 3-Propargyl, 5-MeO | Me | 5'-MeO, 6'-MeO | MeO | |
| 224 | (I-8) | 2-Br, 3-Et, 5-MeO | Me | 5'-MeO, 6'-MeO | MeO | |
| 225 | (I-8) | 2-Br, 3-Allyl, 5-MeO | Me | 5'-MeO, 6'-MeO | MeO | |
| 226 | (I-8) | 2-Br, 3-n-Propyl, 5-MeO | Me | 5'-MeO, 6'-MeO | MeO | |
| 227 | (I-8) | 2-Br, 3-Propargyl, 5-MeO | Me | 5'-MeO, 6'-MeO | MeO | |
| 228 | (I-8) | 3-Me, 5-Br | Me | 5'-MeO, 6'-MeO | MeO | m.p. 88–93° C. |
| 229 | (I-8) | 3-Et, 5-Br | Me | 5'-MeO, 6'-MeO | MeO | |
| 230 | (I-8) | 3-Allyl, 5-Br | Me | 5'-MeO, 6'-MeO | MeO | |
| 231 | (I-8) | 3-n-Propyl, 5-Br | Me | 5'-MeO, 6'-MeO | MeO | |
| 232 | (I-8) | 3-Propargyl, 5-Br | Me | 5'-MeO, 6'-MeO | MeO | |
| 233 | (I-8) | 3-Me, 5-Br, 6-Cl | Me | 5'-MeO, 6'-MeO | MeO | |
| 234 | (I-8) | 3-Et, 5-Br, 6-Cl | Me | 5'-MeO, 6'-MeO | MeO | |

TABLE 16

| No. | Formula | (X)$_n$ | R$^1$ | (R$^2$)$_p$ | R$^3$ | Physical properties |
|---|---|---|---|---|---|---|
| 235 | (I-8) | 3-Allyl, 5-Br, 6-Cl | Me | 5'-MeO, 6'-MeO | MeO | |
| 236 | (I-8) | 3-n-Propyl, 5-Br, 6-Cl | Me | 5'-MeO, 6'-MeO | MeO | |
| 237 | (I-8) | 3-Propargyl, 5-Br, 6-Cl | Me | 5'-MeO, 6'-MeO | MeO | |
| 238 | (I-8) | 3-Me, 5-Br, 6-Br | Me | 5'-MeO, 6'-MeO | MeO | |
| 239 | (I-8) | 3-Et, 5-Br, 6-Br | Me | 5'-MeO, 6'-MeO | MeO | |
| 240 | (I-8) | 3-Allyl, 5-Br, 6-Br | Me | 5'-MeO, 6'-MeO | MeO | |
| 241 | (I-8) | 3-n-Propyl, 5-Br, 6-Br | Me | 5'-MeO, 6'-MeO | MeO | |
| 242 | (I-8) | 3-Propargyl, 5-Br, 6-Br | Me | 5'-MeO, 6'-MeO | MeO | |
| 243 | (I-8) | 3-MeO, 5-MeO | Me | 5'-MeO, 6'-MeO | MeO | Red oily substance |
| 244 | (I-8) | 3-MeO, 5-Cl | Me | 5'-MeO, 6'-MeO | MeO | Pale yellow oily substance |
| 245 | (I-8) | 2-Br, 3-Cl, 5-MeO | Me | 5'-MeO, 6'-MeO | MeO | m.p. 97–99° C. |
| 246 | (I-8) | 2-Br, 3-Br, 5-Br | Me | 5'-MeO, 6'-MeO | MeO | |
| 247 | (I-8) | 2-Cl, 3-Br, 5-Br | Me | 5'-MeO, 6'-MeO | MeO | |
| 248 | (I-8) | 2-Br, 3-Cl, 5-Cl | Me | 5'-MeO, 6'-MeO | MeO | |
| 249 | (I-8) | 2-Cl, 3-MeO, 5-Cl, 6-Cl | Me | 5'-MeO, 6'-MeO | MeO | Yellow oily substance |
| 250 | (I-8) | 2-Br, 3-MeO, 5-Cl, 6-Cl | Me | 5'-MeO, 6'-MeO | MeO | Yellow oily substance |
| 251 | (I-8) | 3-EtO, 5-EtO | Me | 5'-MeO, 6'-MeO | MeO | m.p. 106–109° C. |
| 252 | (I-8) | 3-EtO, 5-Cl | Me | 5'-MeO, 6'-MeO | MeO | m.p. 98.5–99.5° C. |
| 253 | (I-8) | 2-Br, 3-EtO, 5-Cl | Me | 5'-MeO, 6'-MeO | MeO | |
| 254 | (I-8) | 2-Br, 3-Cl, 5-EtO | Me | 5'-MeO, 6'-MeO | MeO | m.p. 113–115° C. |
| 255 | (I-8) | 2-Cl, 3-Br, 5-EtO | Me | 5'-MeO, 6'-MeO | MeO | |
| 256 | (I-8) | 2-Br, 3-Br, 5-EtO | Me | 5'-MeO, 6'-MeO | MeO | |
| 257 | (I-8) | 2-Br, 3-Cl, 5-Cl | Me | 5'-MeO, 6'-MeO | MeO | |
| 258 | (I-8) | 2-Cl, 3-EtO, 5-Cl, 6-Cl | Me | 5'-MeO, 6'-MeO | MeO | |

TABLE 17

| No. | Formula | (X)$_n$ | R$^1$ (R$^2$)$_p$ | R$^3$ | Physical properties |
|---|---|---|---|---|---|
| 259 | (I-8) | 2-Br, 3-EtO, 5-Cl, 6-Cl | Me 5'-MeO, 6'-MeO | MeO | |
| 260 | (I-8) | 2-Cl, 3-EtO, 5-Cl, 6-Br | Me 5'-MeO, 6'-MeO | MeO | |
| 261 | (I-8) | 2-Br, 3-EtO, 5-Cl, 6-Br | Me 5'-MeO, 6'-MeO | MeO | |
| 262 | (I-8) | 2-F, 3-F, 5-F, 6-F | Me 5'-MeO, 6'-MeO | MeO | m.p. 85–87° C. |
| 263 | (I-8) | 2-Br, 3-F, 5-F | Me 5'-MeO, 6'-MeO | MeO | |
| 264 | (I-8) | 2-F, 3-Me, 5-F | Me 5'-MeO, 6'-MeO | MeO | |
| 265 | (I-8) | 2-Br, 3-F, 5-F, 6-Br | Me 5'-MeO, 6'-MeO | MeO | |
| 266 | (I-8) | 2-Cl, 3-F, 5-F | Me 5'-MeO, 6'-MeO | MeO | |
| 267 | (I-8) | 2-Br, 3-Br, 5-Br, 6-Br | Me 5'-MeO, 6'-MeO | MeO | |
| 268 | (I-8) | 2-Cl, 3-Cl, 5-Cl, 6-Cl | Me 5'-MeO, 6'-MeO | MeO | |
| 269 | (I-8) | 3-Br, 5-F | Me 5'-MeO, 6'-MeO | MeO | |
| 270 | (I-8) | 2-Br, 3-F, 5-F, 6-F | Me 5'-MeO, 6'-MeO | MeO | |
| 271 | (I-8) | 3-F, 5-CH$_3$ | Me 5'-MeO, 6'-MeO | MeO | |
| 272 | (I-8) | 3-Cl, 5-CH$_3$ | Me 5'-MeO, 6'-MeO | MeO | m.p. 84–88° C. |
| 273 | (I-8) | 3-F, 5-MeO | Me 5'-MeO, 6'-MeO | MeO | |
| 274 | (I-8) | 2-Cl, 3-CF$_3$, 6-CF$_3$ | Me 5'-MeO, 6'-MeO | MeO | m.p. 85–88° C. |
| 275 | (I-8) | 3-CF$_3$, 6-CF$_3$ | Me 5'-MeO, 6'-MeO | MeO | |
| 276 | (I-8) | 3-CF$_3$, 5-Me, 6-CF$_3$ | Me 5'-MeO, 6'-MeO | MeO | |
| 277 | (I-8) | 3-CF$_3$, 5-Et, 6-CF$_3$ | Me 5'-MeO, 6'-MeO | MeO | |
| 278 | (I-8) | 3-CF$_3$, 5-Allyl, 6-CF$_3$ | Me 5'-MeO, 6'-MeO | MeO | |
| 279 | (I-8) | 3-CF$_3$, 5-n-Propyl, 6-CF$_3$ | Me 5'-MeO, 6'-MeO | MeO | |
| 280 | (I-8) | 3-CF$_3$, 5-Propargyl, 6-CF$_3$ | Me 5'-MeO, 6'-MeO | MeO | |
| 281 | (I-8) | 2-Cl, 3-CF$_3$, 5-CF$_3$, 6-Cl | Me 5'-MeO, 6'-MeO | MeO | |
| 282 | (I-8) | 2-Cl, 3-CF$_3$, 5-CF$_3$ | Me 5'-MeO, 6'-MeO | MeO | |

TABLE 18

| No. | Formula | (X)$_n$ | R$^1$ (R$^2$)$_p$ | R$^3$ | Physical properties |
|---|---|---|---|---|---|
| 283 | (I-8) | 3-CF$_3$, 5-CF$_3$ | Me 5'-MeO, 6'-MeO | MeO | |
| 284 | (I-9) | 3-Cl, 5-Cl, 6-Cl | Me 5'-MeO, 6'-MeO | MeO | m.p. 144–147° C. |
| 285 | (I-9) | 3-F, 5-F, 6-F | Me 5'-MeO, 6'-MeO | MeO | |
| 286 | (I-9) | 3-Br, 5-Br | Me 5'-MeO, 6'-MeO | MeO | Pale yellow oily substance |
| 287 | (I-1) | 2-MeO | Me 5'-C-Hexyl—O | MeO | m.p. 97–100° C. |
| 288 | (I-8) | 2-Me, 3-Cl, 6-Cl | Me 5'-MeO | MeO | m.p. 111–113° C. |
| 289 | (I-8) | 2-Me, 3-Cl, 6-Cl | Et 5'-MeO | MeO | m.p. 88–94° C. |
| 290 | (I-8) | 2-Me, 3-Cl | Me 5'-MeO | MeO | m.p. 117–118° C. |
| 291 | (I-8) | 2-Cl, 3-Br, 5-MeO | Me 5'-MeO, 6'-MeO | MeO | Brown oily substance |
| 292 | (I-8) | 2-Br, 3-Br, 5-MeO | Me 5'-MeO, 6'-MeO | MeO | Yellow oily substance |

Compounds represented by the formula (X) to be used as an intermediate, produced by processes in accordance with Synthesis Examples 1, 3, 5, 6, 8, 9, 11 and 16, are shown in the following Tables 19 to 36.

Here, compounds represented by the general formulae (X-1) to (X-9) in Tables are the following compounds.

Further, in Tables, Me represents a methyl group, Et represents an ethyl group, Butyl represents a butyl group, i-Propyl represents an isopropyl group, Ph represents a phenyl group, Allyl represents an allyl group, c-Hexyl represents a cyclohexyl group, Benzyl represents a benzyl group, Propargyl represents a propargyl group, and Pentyl represents a pentyl group.

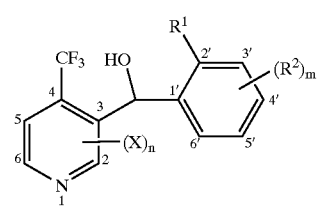

(X-1)

-continued

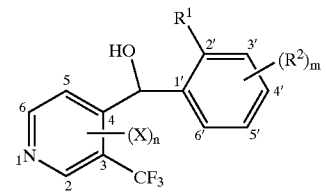
(X-2)

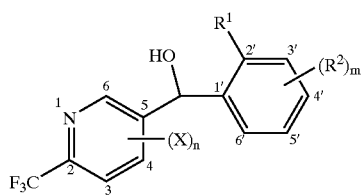
(X-3)

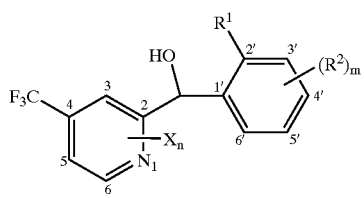
(X-4)

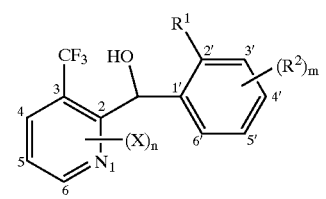
(X-5)

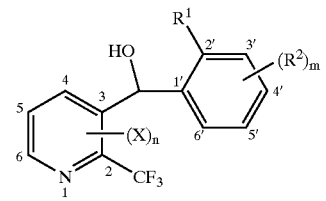
(X-6)

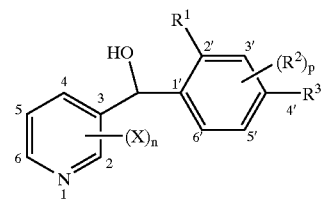
(X-7)

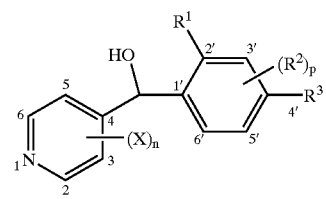
(X-8)

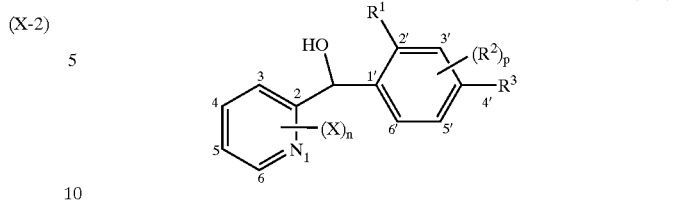
(X-9)

TABLE 19

Compounds represented by Formula (X-1)

| No. | $(X)_n$ | $R^1$ | $(R^2)_m$ | Physical properties |
|---|---|---|---|---|
| 1 | 2-Cl, 6-Cl | Me | 4'-MeO, 5'-MeO | Viscous substance |
| 2 | 2-Cl, 6-Cl | Me | 4'-MeO, 5'-Me | Viscous substance |
| 3 | 2-Cl, 6-Cl | Me | 4'-MeO, 5'-MeO, 6'-MeO | Viscous substance |
| 4 | 2-Cl, 6-Cl | Me | 4'-MeO | Viscous substance |
| 5 | Not substituted | Me | 4'-MeO, 5'-MeO | |
| 6 | Not substituted | Me | 4'-MeO, 5'-Me | |
| 7 | Not substituted | Me | 4'-MeO, 5'-MeO, 6'-MeO | m.p. 132–135° C. |
| 8 | Not substituted | Me | 4'-MeO | |
| 9 | 2-Cl | Me | 4'-MeO, 5'-MeO | |
| 10 | 2-Cl | Me | 4'-MeO, 5'-Me | |
| 11 | 2-Cl | Me | 4'-MeO, 5'-MeO, 6'-MeO | Viscous substance |
| 12 | 2-Cl | Me | 4'-Me, 5'-Me, 6'-Me | m.p. 125–127° C. |
| 13 | 2-Cl | Me | 4', 5'-(—OCH$_2$O—) | m.p. 127–130° C. |
| 14 | 2-Cl | Me | 4'-MeO | |
| 15 | 2-Cl | Et | 4'-MeO, 5'-MeO, 6'-MeO | |
| 16 | 2-Cl | i-Propyl | 4'-MeO, 5'-MeO, 6'-MeO | |
| 17 | 2-Cl | Me | 3'-MeO, 4'-MeO, 5'-MeO, 6'-MeO | |
| 18 | 2-Cl | Me | 4'-MeO, 5'-EtO | Viscous substance |
| 19 | 2-Cl | Me | 4'-MeO, 5'-i-Propyl—O— | Viscous substance |
| 20 | 2-Cl | Me | 4'-MeO, 5'-Allyl—O— | |
| 21 | 2-Cl | Me | 4'-MeO, 5'-Propargyl—O— | |
| 22 | 2-Cl | Me | 4'-MeO, 5'-CF$_3$CH$_2$O— | |
| 23 | 2-Cl | Me | 4'-MeO, 5'-c-Hexyl—O— | Viscous substance |

TABLE 20

Compounds represented by Formula (X-1)

| No. | $(X)_n$ | $R^1$ | $(R^2)_m$ | Physical properties |
|---|---|---|---|---|
| 24 | 2-Cl | Me | 4'-MeO, 5'-(CH$_3$)$_2$N(CH$_2$)$_2$O— | |
| 25 | 2-Cl | Me | 4'-MeO, 5'-CH$_3$S(CH$_2$)$_2$O— | |
| 26 | 2-Cl | Me | 4'-MeO, 5'-PhO— | |
| 27 | 2-Cl | Me | 4'-MeO, 5'-Benzyl—O— | Viscous substance |
| 28 | 2-Cl | Me | 4'-MeO, 5'-CH$_3$COO— | |
| 29 | 2-Cl | Me | 4'-MeO, 5'-CH$_3$OCOO— | |
| 30 | 2-MeO, 6-MeO | Me | 4'-MeO, 5'-MeO, 6'-MeO | |
| 31 | 2-Cl, 6-MeO | Me | 4'-MeO, 5'-MeO, 6'-MeO | |
| 32 | 2-MeO | Me | 4'-MeO, 5'-MeO | |
| 33 | 2-i-Propyl—O— | Me | 4'-MeO, 5'-MeO, 6'-MeO | |
| 34 | 2-CF$_3$CH$_2$O— | Me | 4'-MeO, 5'-MeO, 6'-MeO | |
| 35 | 2-CH$_3$O(CH$_2$)$_2$O— | Me | 4'-MeO, 5'-MeO, 6'-MeO | |
| 36 | 2-CH$_3$S(CH$_2$)$_2$O— | Me | 4'-MeO, 5'-MeO, 6'-MeO | |
| 37 | 2-PhO— | Me | 4'-MeO, 5'-MeO, 6'-MeO | |
| 38 | 2-Benzyl—O— | Me | 4'-MeO, 5'-MeO, 6'-MeO | |
| 39 | 2-c-Hexyl—O— | Me | 4'-MeO, 5'-MeO, 6'-MeO | |
| 40 | 2-Allyl—O— | Me | 4'-MeO, 5'-MeO, 6'-MeO | |
| 41 | 2-Propargyl—O— | Me | 4'-MeO, 5'-MeO, 6'-MeO | |
| 42 | 2-(CH$_3$)$_2$N(CH$_2$)$_2$O— | Me | 4'-MeO, 5'-MeO, 6'-MeO | |
| 43 | 2-Cl, 5-Me | Me | 4'-MeO, 5'-MeO, 6'-MeO | |
| 44 | 2-Cl, 5-Allyl | Me | 4'-MeO, 5'-MeO, 6'-MeO | |
| 45 | 2-Cl, 5-Propargyl | Me | 4'-MeO, 5'-MeO, 6'-MeO | |
| 46 | 2-Cl, 5-CH$_3$O(C=O)— | Me | 4'-MeO, 5'-MeO, 6'-MeO | |
| 47 | 2-Cl, 5-CH$_3$(C=O)— | Me | 4'-MeO, 5'-MeO, 6'-MeO | |

TABLE 21

Compounds represented by Formula (X-1)

| No. | $(X)_n$ | $R^1$ | $(R^2)_m$ | Physical properties |
|---|---|---|---|---|
| 48 | 2-Cl, 5-Et | Me | 4'-MeO, 5'-MeO, 6'-MeO | |
| 49 | 2-MeO, 5-Me | Me | 4'-MeO, 5'-MeO, 6'-MeO | |
| 50 | 2-MeS | Me | 4'-MeO, 5'-MeO, 6'-MeO | |
| 51 | 2-Me$_2$N | Me | 4'-MeO, 5'-MeO, 6'-MeO | |
| 52 | 2-Cl, 5-(CH$_3$)$_2$N(C=O)— | Me | 4'-MeO, 5'-MeO, 6'-MeO | |
| 53 | 2-CN | Me | 4'-MeO, 5'-MeO, 6'-MeO | |
| 54 | 2-Cl, 5-Cl, 6-Cl | Me | 4'-MeO, 5'-MeO, 6'-MeO | Viscous substance |
| 55 | 2-Cl, 5-Cl | Me | 4'-MeO, 5'-MeO, 6'-MeO | |
| 56 | 2-MeO, 5-Cl | Me | 4'-MeO, 5'-MeO, 6'-MeO | |
| 57 | 2-OH, 5-Cl | Me | 4'-MeO, 5'-MeO, 6'-MeO | |
| 58 | 2-Cl, 5-Me, 6-Cl | Me | 4'-MeO, 5'-MeO, 6'-MeO | Viscous substance |
| 59 | 2-Cl, 5-Allyl, 6-Cl | Me | 4'-MeO, 5'-MeO, 6'-MeO | Viscous substance |
| 60 | 2-Cl, 5-Propargyl, 6-Cl | Me | 4'-MeO, 5'-MeO, 6'-MeO | |
| 61 | 2-Cl, 5-CH$_3$O(C=O)—, 6-Cl | Me | 4'-MeO, 5'-MeO, 6'-MeO | m.p. 133–135° C. |
| 62 | 2-Cl, 5-CH$_3$CH(OH)—, 6-Cl | Me | 4'-MeO, 5'-MeO, 6'-MeO | m.p. 141–158° C. |
| 63 | 2-Cl, 5-Et, 6-Cl | Me | 4'-MeO, 5'-MeO, 6'-MeO | |
| 64 | 2-Cl, 5-(CH$_3$)$_2$N(C=O)— | Me | 4'-MeO, 5'-MeO, 6'-MeO | |
| 65 | 5-Me | Me | 4'-MeO, 5'-MeO, 6'-MeO | |
| 66 | 5-Allyl | Me | 4'-MeO, 5'-MeO, 6'-MeO | |
| 67 | 5-Propargyl | Me | 4'-MeO, 5'-MeO, 6'-MeO | |
| 68 | 5-CH$_3$O(C=O)— | Me | 4'-MeO, 5'-MeO, 6'-MeO | |
| 69 | 5-CH$_3$(C=O)— | Me | 4'-MeO, 5'-MeO, 6'-MeO | |
| 70 | 5-Et | Me | 4'-MeO, 5'-MeO, 6'-MeO | |

TABLE 22

Compounds represented by Formula (X-1)

| No. | (X)$_n$ | R$^1$ | (R$^2$)$_m$ | Physical properties |
|---|---|---|---|---|
| 71 | 5-(CH$_3$)$_2$N(C=O)— | Me | 4'-MeO, 5'-MeO, 6'-MeO | |
| 72 | 2-CH$_3$O(CH$_2$)$_2$O— | Me | 4'-MeO, 5'-MeO | |
| 73 | 2-(6'-phenyl)—O— | Me | 4'-MeO, 5'-MeO, 6'-O-(2-Pyridyl) | |
| 74 | 2-MeO | Me | 4'-MeO, 5'-MeO, 6'-MeO | |
| 75 | 2-EtO | Me | 4'-MeO, 5'-MeO, 6'-MeO | |
| 76 | 2-MeS | Me | 4'-MeO, 5'-MeO, 6'-OH | |
| 77 | 2-OH | Me | 4'-MeO, 5'-MeO, 6'-MeO | |
| 78 | 2-NH$_2$ | Me | 4'-MeO, 5'-MeO, 6'-MeO | |
| 79 | 2-CH$_3$NH | Me | 4'-MeO, 5'-MeO, 6'-MeO | |
| 80 | 2-CH$_3$COO | Me | 4'-MeO, 5'-MeO, 6'-MeO | |
| 81 | 2-i-Propyl—O | Me | 4'-MeO, 5'-MeO, 6'-i-Propyl—O | |
| 82 | 2-Cl, 6-Cl | Et | 4'-MeO, 5'-MeO, 6'-MeO | |
| 83 | 2-Cl | Me | 4'-MeO, 5'-(4-MeO—Benzyl)O | Viscous substance |
| 84 | 2-Me | Me | 4'-MeO, 5'-MeO, 6'-MeO | |
| 85 | 2-Me, 5-Cl | Me | 4'-MeO, 5'-MeO, 6'-MeO | |
| 86 | 2-Me, 5-Br | Me | 4'-MeO, 5'-MeO, 6'-MeO | |

TABLE 23

Compounds represented by Formula (X-2)

| No. | (X)$_n$ | R$^1$ | (R$^2$)$_m$ | Physical properties |
|---|---|---|---|---|
| 87 | 2-PhO, 5-Cl | Me | 4'-MeO, 5'-MeO, 6'-MeO | |
| 88 | 2-OH, 5-Cl | Me | 4'-MeO, 5'-MeO, 6'-MeO | |

TABLE 24

Compounds represented by Formula (X-2)

| No. | (X)$_n$ | R$^1$ | (R$^2$)$_m$ | Physical properties |
|---|---|---|---|---|
| 89 | 2-Cl, 5-Cl | Me | 4'-MeO, 5'-MeO | m.p.134–136° C. |
| 90 | 2-Cl, 5-Cl | Me | 4'-MeO, 5'-MeO, 6'-MeO | m.p.162–165° C. |
| 91 | Not substituted | Me | 4'-MeO, 5'-MeO | |
| 92 | Not substituted | Me | 4'-MeO, 5'-MeO, 6'-MeO | m.p.101–106° C. |
| 93 | 2-MeO, 5-Cl | Me | 4'-MeO, 5'-MeO, 6'-MeO | |
| 94 | 2-MeO 5-Cl | Me | 4'-MeO, 5'-MeO | |
| 95 | 2-Br, 5-Cl | Me | 4'-MeO, 5'-MeO, 6'-MeO | |
| 96 | 2-MeS, 5-Cl | Me | 4'-MeO, 5'-MeO, 6'-MeO | |
| 97 | 2-CN, 5-Cl | Me | 4'-MeO, 5'-MeO, 6'-MeO | |
| 98 | 2-Cl, 5-Cl, 6-Cl | Me | 4'-MeO, 5'-MeO | m.p.156–158° C. |
| 99 | 2-Cl, 5-Cl, 6-Cl | Me | 4'-MeO, 5'-MeO, 6'-MeO | m.p.131–135° C. |
| 100 | 5-Cl, 6-Cl | Me | 4'-MeO, 5'-MeO | Viscous substance |
| 101 | 5-Cl | Me | 4'-MeO, 5'-MeO | |
| 102 | 5-Cl | Me | 4'-MeO, 5'-MeO, 6'-MeO | m.p.102–105° C. |
| 103 | 5-Cl, 6-Cl | Me | 4'-MeO, 5'-MeO, 6'-MeO | m.p.95–98° C. |
| 104 | 5-Cl, 6-MeO | Me | 4'-MeO, 5'-MeO, 6'-MeO | |
| 105 | 5-Cl, 6-MeO | Me | 4'-MeO, 5'-MeO | |
| 106 | 5-Cl, 6-EtO | Me | 4'-MeO, 5'-MeO, 6'-MeO | |
| 107 | 6-MeO | Me | 4'-MeO, 5'-MeO, 6'-MeO | |
| 108 | 5-Cl, 6-n-Propyl—O | Me | 4'-MeO, 5'-MeO, 6'-MeO | |
| 109 | 6-EtO | Me | 4'-MeO, 5'-MeO, 6'-MeO | |
| 110 | 5-Cl, 6-n-Butyl—O | Me | 4'-MeO, 5'-MeO, 6'-MeO | |
| 111 | 6-n-Propyl—O | Me | 4'-MeO, 5'-MeO, 6'-MeO | |
| 112 | 6-n-Butyl—O | Me | 4'-MeO, 5'-MeO, 6'-MeO | |

TABLE 25

Compounds represented by Formula (X-2)

| No. | (X)$_n$ | R$^1$ | (R$^2$)$_m$ | Physical properties |
|---|---|---|---|---|
| 113 | 5-Cl, 6-Propargyl—O | Me | 4'-MeO, 5'-MeO, 6'-MeO | |
| 114 | 5-Cl, 6-n-Pentyl—O | Me | 4'-MeO, 5'-MeO, 6'-MeO | |
| 115 | 5-Cl, 6-OH | Me | 4'-MeO, 5'-MeO, 6'-MeO | |
| 116 | 6-n-Pentyl—O | Me | 4'-MeO, 5'-MeO, 6'-MeO | |
| 117 | 5-Cl, 6-CH$_3$S(CH$_2$)$_2$O | Me | 4'-MeO, 5'-MeO, 6'-MeO | |
| 118 | 5-Cl, 6-Allyl—O | Me | 4'-MeO, 5'-MeO, 6'-MeO | |
| 119 | 5-Cl, 6-CH$_3$O(CH$_2$)$_2$O | Me | 4'-MeO, 5'-MeO, 6'-MeO | |
| 120 | 2-MeO, 5-MeO | Me | 4'-MeO, 5'-MeO, 6'-MeO | |
| 121 | 2-MeO | Me | 4'-MeO, 5'-MeO, 6'-MeO | |
| 122 | 5-MeO | Me | 4'-MeO, 5'-MeO, 6'-MeO | |
| 123 | 2-Cl, 5-MeO | Me | 4'-MeO, 5'-MeO, 6'-MeO | |
| 124 | 2-Br, 5-MeO | Me | 4'-MeO, 5'-MeO, 6'-MeO | |
| 125 | 2-Me, 5-MeO | Me | 4'-MeO, 5'-MeO, 6'-MeO | |
| 126 | 2-Et, 5-MeO | Me | 4'-MeO, 5'-MeO, 6'-MeO | |
| 127 | 2-n-Propyl, 5-MeO | Me | 4'-MeO, 5'-MeO, 6'-MeO | |
| 128 | 2-Allyl, 5-MeO | Me | 4'-MeO, 5'-MeO, 6'-MeO | |
| 129 | 2-Propargyl, 5-MeO | Me | 4'-MeO, 5'-MeO, 6'-MeO | |
| 130 | 2-EtO, 5-MeO | Me | 4'-MeO, 5'-MeO, 6'-MeO | |
| 131 | 2-CN, 5-MeO | Me | 4'-MeO, 5'-MeO, 6'-MeO | |
| 132 | 2-MeS, 5-MeO | Me | 4'-MeO, 5'-MeO, 6'-MeO | |
| 133 | 5-Me | Me | 4'-MeO, 5'-MeO, 6'-MeO | |
| 134 | 5-Br | Me | 4'-MeO, 5'-MeO, 6'-MeO | |
| 135 | 5-F | Me | 4'-MeO, 5'-MeO, 6'-MeO | |

TABLE 26

Compound represented by Formula (X-3)

| No. | (X)$_n$ | R$^1$ | (R$^2$)$_m$ | Physical properties |
|---|---|---|---|---|
| 136 | 6-Cl | Me | 4'-MeO, 5'-MeO, 6'-MeO | Viscous substance |

TABLE 27

Compound represented by Formula (X-4)

| No. | (X)$_n$ | R$^1$ | (R$^2$)$_m$ | Physical properties |
|---|---|---|---|---|
| 137 | Not substituted | Me | 4'-MeO, 5'-MeO, 6'-MeO | |

TABLE 28

Compound represented by Formula (X-5)

| No. | (X)$_n$ | R$^1$ | (R$^2$)$_m$ | Physical properties |
|---|---|---|---|---|
| 138 | 5-Cl, 6-Cl | Me | 4'-MeO, 5'-MeO, 6'-MeO | m.p. 71–73° C. |

TABLE 29

Compounds represented by Formula (X-6)

| No. | (X)$_n$ | R$^1$ | (R$^2$)$_m$ | Physical properties |
|---|---|---|---|---|
| 139 | 4-Me | Me | 4'-MeO, 5'-MeO, 6'-MeO | |
| 140 | 4-Me, 5-Cl | Me | 4'-MeO, 5'-MeO, 6'-MeO | |
| 141 | 4-Me, 5-Br | Me | 4'-MeO, 5'-MeO, 6'-MeO | |

TABLE 30

| No. | Formula | (X)$_n$ | R$^1$ | (R$^2$)$_p$ | R$^3$ | Physical properties |
|---|---|---|---|---|---|---|
| 142 | (X-7) | 2-MeO | Me | 5'-MeO | MeO | Viscous substance |
| 143 | (X-7) | 2-Cl, 4-Cl | Me | 5'-MeO | PhO | |
| 144 | (X-7) | 2-Cl, 4-Cl | Me | 5'-MeO, 6'-MeO | MeO | |
| 145 | (X-7) | 2-Cl, 4-MeO | Me | 5'-MeO, 6'-MeO | MeO | |
| 146 | (X-7) | 2-MeO, 4-Cl | Me | 5'-MeO, 6'-MeO | MeO | |
| 147 | (X-7) | 2-F, 4-F | Me | 5'-MeO, 6'-MeO | MeO | |
| 148 | (X-7) | 2-F, 4-MeO | Me | 5'-MeO, 6'-MeO | MeO | |
| 149 | (X-7) | 2-MeO, 4-F | Me | 5'-MeO, 6'-MeO | MeO | |
| 150 | (X-7) | 2-Cl, 4-Cl, 5-Cl | Me | 5'-MeO, 6'-MeO | MeO | |
| 151 | (X-7) | 2-Me, 4-Me | Me | 5'-MeO, 6'-MeO | MeO | |
| 152 | (X-7) | 2-Me, 4-Me, 5-Cl | Me | 5'-MeO, 6'-MeO | MeO | |
| 153 | (X-7) | 2-Me, 4-Me, 5-Br | Me | 5'-MeO, 6'-MeO | MeO | |
| 154 | (X-7) | 2-Me, 4-MeO | Me | 5'-MeO, 6'-MeO | MeO | |
| 155 | (X-7) | 2-Me, 4-MeO, 5-Cl | Me | 5'-MeO, 6'-MeO | MeO | |
| 156 | (X-7) | 2-Me, 4-MeO, 5-Br | Me | 5'-MeO, 6'-MeO | MeO | |
| 157 | (X-7) | 2-MeO, 4-Me | Me | 5'-MeO, 6'-MeO | MeO | |
| 158 | (X-7) | 2-MeO, 4-Me, 5-Cl | Me | 5'-MeO, 6'-MeO | MeO | |
| 159 | (X-7) | 2-MeO, 4-Me, 5-Br | Me | 5'-MeO, 6'-MeO | MeO | |
| 160 | (X-7) | 2-Me, 4-Cl | Me | 5'-MeO, 6'-MeO | MeO | |
| 161 | (X-7) | 2-Me, 4-Cl, 5-Cl | Me | 5'-MeO, 6'-MeO | MeO | |
| 162 | (X-7) | 2-Me, 4-Cl, 5-Br | Me | 5'-MeO, 6'-MeO | MeO | |
| 163 | (X-7) | 2-Cl, 4-Me | Me | 5'-MeO, 6'-MeO | MeO | |
| 164 | (X-7) | 2-Cl, 4-Me, 5-Cl | Me | 5'-MeO, 6'-MeO | MeO | |
| 165 | (X-7) | 2-Cl, 4-Me, 5-Br | Me | 5'-MeO, 6'-MeO | MeO | |
| 166 | (X-7) | 2-CF$_3$, 4-CF$_3$, 6-Cl | Me | 5'-MeO, 6'-MeO | MeO | |

TABLE 31

| No. | Formula | (X)$_n$ | R$^1$ | (R$^2$)$_p$ | R$^3$ | Physical properties |
|---|---|---|---|---|---|---|
| 167 | (X-7) | 2-Cl, 4-CF$_3$, 6-CF$_3$ | Me | 5'-MeO, 6'-MeO | MeO | Viscous substance |
| 168 | (X-7) | 2-CF$_3$, 4-CF$_3$, 5-Me | Me | 5'-MeO, 6'-MeO | MeO | |
| 169 | (X-7) | 2-CF$_3$, 4-CF$_3$, 5-Et | Me | 5'-MeO, 6'-MeO | MeO | |
| 170 | (X-7) | 2-CF$_3$, 4-CF$_3$, 5-Allyl | Me | 5'-MeO, 6'-MeO | MeO | |
| 171 | (X-7) | 2-CF$_3$, 4-CF$_3$, 5-n-Propyl | Me | 5'-MeO, 6'-MeO | MeO | |
| 172 | (X-7) | 2-CF$_3$, 4-CF$_3$, 5-Propargyl | Me | 5'-MeO, 6'-MeO | MeO | |
| 173 | (X-7) | 2-CF$_3$, 4-CF$_3$, 5-Me, 6-Cl | Me | 5'-MeO, 6'-MeO | MeO | |
| 174 | (X-7) | 2-CF$_3$, 4-CF$_3$, 5-Et, 6-Cl | Me | 5'-MeO, 6'-MeO | MeO | |
| 175 | (X-7) | 2-CF$_3$, 4-CF$_3$, 5-Allyl, 6-Cl | Me | 5'-MeO, 6'-MeO | MeO | |
| 176 | (X-7) | 2-CF$_3$, 4-CF$_3$, 5-n-Propyl, 6-Cl | Me | 5'-MeO, 6'-MeO | MeO | |
| 177 | (X-7) | 2-CF$_3$, 4-CF$_3$, 5-Propargyl, 6-Cl | Me | 5'-MeO, 6'-MeO | MeO | |
| 178 | (X-7) | 2-CF$_3$, 4-CF$_3$ | Me | 5'-MeO, 6'-MeO | MeO | |
| 179 | (X-7) | 2-CF$_3$, 5-CF$_3$, 6-Cl | Me | 5'-MeO, 6'-MeO | MeO | |
| 180 | (X-7) | 2-CF$_3$, 5-CF$_3$ | Me | 5'-MeO, 6'-MeO | MeO | |
| 181 | (X-7) | 2-CF$_3$, 4-Me, 5-CF$_3$ | Me | 5'-MeO, 6'-MeO | MeO | |
| 182 | (X-7) | 2-CF$_3$, 4-Et, 5-CF$_3$ | Me | 5'-MeO, 6'-MeO | MeO | |
| 183 | (X-7) | 2-CF$_3$, 4-Allyl, 5-CF$_3$ | Me | 5'-MeO, 6'-MeO | MeO | |
| 184 | (X-7) | 2-CF$_3$, 4-n-propyl, 5-CF$_3$ | Me | 5'-MeO, 6'-MeO | MeO | |
| 185 | (X-7) | 2-CF$_3$, 4-propargyl, 5-CF$_3$ | Me | 5'-MeO, 6'-MeO | MeO | |

TABLE 31-continued

| No. | Formula | (X)$_n$ | R$^1$ | (R$^2$)$_p$ | R$^3$ | Physical properties |
|---|---|---|---|---|---|---|
| 186 | (X-8) | 2-Cl, 3-Cl, 5-Cl | Me | 5'-MeO, 6'-MeO | MeO | Amorphous |
| 187 | (X-8) | 2-MeO, 3-Cl, 5-Cl | Me | 5'-MeO, 6'-MeO | MeO | |

TABLE 32

| No. | Formula | (X)$_n$ | R$^1$ | (R$^2$)$_p$ | R$^3$ | Physical properties |
|---|---|---|---|---|---|---|
| 188 | (X-8) | 2-EtO, 3-Cl, 5-Cl | Me | 5'-MeO, 6'-MeO | MeO | |
| 189 | (X-8) | 2-MeO, 3-MeO, 5-Cl | Me | 5'-MeO, 6'-MeO | MeO | |
| 190 | (X-8) | 2-MeO, 3-MeO | Me | 5'-MeO, 6'-MeO | MeO | |
| 191 | (X-8) | 3-Cl, 5-Cl | Me | 5'-MeO, 6'-MeO | MeO | m.p. 136–140° C. |
| 192 | (X-8) | 3-Cl | Me | 5'-MeO, 6'-MeO | MeO | m.p. 160–162° C. |
| 193 | (X-8) | 2-Cl, 3-Cl, 5-MeO | Me | 5'-MeO, 6'-MeO | MeO | |
| 194 | (X-8) | 2-Cl, 3-Cl, 5-EtO | Me | 5'-MeO, 6'-MeO | MeO | |
| 195 | (X-8) | 2-Cl, 3-MeO, 5-MeO | Me | 5'-MeO, 6'-MeO | MeO | |
| 196 | (X-8) | 2-Cl, 3-EtO, 5-MeO | Me | 5'-MeO, 6'-MeO | MeO | |
| 197 | (X-8) | 3-MeO | Me | 5'-MeO, 6'-MeO | MeO | |
| 198 | (X-8) | 3-EtO | Me | 5'-MeO, 6'-MeO | MeO | |
| 199 | (X-8) | 2-Cl, 3-MeO, 5-Cl | Me | 5'-MeO, 6'-MeO | MeO | |
| 200 | (X-8) | 2-Cl, 3-EtO, 5-Cl | Me | 5'-MeO, 6'-MeO | MeO | |
| 201 | (X-8) | 3-Br | Me | 5'-MeO, 6'-MeO | MeO | m.p. 168–169° C. |
| 202 | (X-8) | 3-Br, 5-Br | Me | 5'-MeO, 6'-MeO | MeO | Viscous substance |
| 203 | (X-8) | 3-Br, 5-MeO | Me | 5'-MeO, 6'-MeO | MeO | m.p. 90–93° C. |
| 204 | (X-8) | 2-F, 3-F, 5-F | Me | 5'-MeO, 6'-MeO | MeO | |
| 205 | (X-8) | 2-MeO, 3-F, 5-F | Me | 5'-MeO, 6'-MeO | MeO | |
| 206 | (X-8) | 2-EtO, 3-F, 5-F | Me | 5'-MeO, 6'-MeO | MeO | |
| 207 | (X-8) | 2-MeO, 3-MeO, 5-F | Me | 5'-MeO, 6'-MeO | MeO | |
| 208 | (X-8) | 3-F, 5-F | Me | 5'-MeO, 6'-MeO | MeO | |
| 209 | (X-8) | 3-F | Me | 5'-MeO, 6'-MeO | MeO | |
| 210 | (X-8) | 3-Me, 5-MeO | Me | 5'-MeO, 6'-MeO | MeO | |

| No. | Formula | (X)$_n$ | R$^1$ | (R$^2$)$_p$ | R$^3$ | Physical properties |
|---|---|---|---|---|---|---|
| 211 | (X-8) | 2-Cl, 3-Me, 5-MeO | Me | 5'-MeO, 6'-MeO | MeO | |
| 212 | (X-8) | 2-Br, 3-Me, 5-MeO | Me | 5'-MeO, 6'-MeO | MeO | |
| 213 | (X-8) | 3-Me, 5-Me | Me | 5'-MeO, 6'-MeO | MeO | |
| 214 | (X-8) | 2-Cl, 3-Me, 5-Me | Me | 5'-MeO, 6'-MeO | MeO | |
| 215 | (X-8) | 2-Br, 3-Me, 5-Me | Me | 5'-MeO, 6'-MeO | MeO | |
| 216 | (X-8) | 3-Et, 5-MeO | Me | 5'-MeO, 6'-MeO | MeO | |
| 217 | (X-8) | 3-Allyl, 5-MeO | Me | 5'-MeO, 6'-MeO | MeO | |
| 218 | (X-8) | 3-n-Propyl, 5-MeO | Me | 5'-MeO, 6'-MeO | MeO | |
| 219 | (X-8) | 3-Propargyl, 5-MeO | Me | 5'-MeO, 6'-MeO | MeO | |
| 220 | (X-8) | 2-Cl, 3-Et, 5-MeO | Me | 5'-MeO, 6'-MeO | MeO | |
| 221 | (X-8) | 2-Cl, 3-Allyl, 5-MeO | Me | 5'-MeO, 6'-MeO | MeO | |
| 222 | (X-8) | 2-Cl, 3-n-Propyl, 5-MeO | Me | 5'-MeO, 6'-MeO | MeO | |
| 223 | (X-8) | 2-Cl, 3-Propargyl, 5-MeO | Me | 5'-MeO, 6'-MeO | MeO | |
| 224 | (X-8) | 2-Br, 3-Et, 5-MeO | Me | 5'-MeO, 6'-MeO | MeO | |
| 225 | (X-8) | 2-Br, 3-Allyl, 5-MeO | Me | 5'-MeO, 6'-MeO | MeO | |
| 226 | (X-8) | 2-Br, 3-n-Propyl, 5-MeO | Me | 5'-MeO, 6'-MeO | MeO | |
| 227 | (X-8) | 2-Br, 3-Propargyl, 5-MeO | Me | 5'-MeO, 6'-MeO | MeO | |
| 228 | (X-8) | 3-Me, 5-Br | Me | 5'-MeO, 6'-MeO | MeO | Viscous substance |
| 229 | (X-8) | 3-Et, 5-Br | Me | 5'-MeO, 6'-MeO | MeO | |
| 230 | (X-8) | 3-Et, 5-Br | Me | 5'-MeO, 6'-MeO | MeO | |
| 231 | (X-8) | 3-n-Propyl, 5-Br | Me | 5'-MeO, 6'-MeO | MeO | |
| 232 | (X-8) | 3-Propargyl, 5-Br | Me | 5'-MeO, 6'-MeO | MeO | |
| 233 | (X-8) | 3-Me, 5-Br, 6-Cl | Me | 5'-MeO, 6'-MeO | MeO | |
| 234 | (X-8) | 3-Et, 5-Br, 6-Cl | Me | 5'-MeO, 6'-MeO | MeO | |

TABLE 35

| No. | Formula | $(X)_n$ | $R^1$ | $(R^2)_p$ | $R^3$ | Physical properties |
|---|---|---|---|---|---|---|
| 259 | (X-8) | 2-Br, 3-EtO, 5-Cl, 6-Cl | Me | 5'-MeO, 6'-MeO | MeO | |
| 260 | (X-8) | 2-Cl, 3-EtO, 5-Cl, 6-Br | Me | 5'-MeO, 6'-MeO | MeO | |
| 261 | (X-8) | 2-Br, 3-EtO, 5-Cl, 6-Br | Me | 5'-MeO, 6'-MeO | MeO | |
| 262 | (X-8) | 2-F, 3-F, 5-F, 6-F | Me | 5'-MeO, 6'-MeO | MeO | Viscous substance |
| 263 | (X-8) | 2-Br, 3-F, 5-F | Me | 5'-MeO, 6'-MeO | MeO | |
| 264 | (X-8) | 2-F, 3-Me, 5-F | Me | 5'-MeO, 6'-MeO | MeO | |
| 265 | (X-8) | 2-Br, 3-F, 5-F, 6-Br | Me | 5'-MeO, 6'-MeO | MeO | |
| 266 | (X-8) | 2-Cl, 3-F, 5-F | Me | 5'-MeO, 6'-MeO | MeO | |
| 267 | (X-8) | 2-Br, 3-Br, 5-Br, 6-Br | Me | 5'-MeO, 6'-MeO | MeO | |
| 268 | (X-8) | 2-Cl, 3-Cl, 5-Cl, 6-Cl | Me | 5'-MeO, 6-MeO | MeO | |
| 269 | (X-8) | 3-Br, 5-F | Me | 5'-MeO, 6'-MeO | MeO | |
| 270 | (X-8) | 2-Br, 3-F, 5-F, 6-F | Me | 5'-MeO, 6'-MeO | MeO | |
| 271 | (X-8) | 3-F, 5-$CH_3$ | Me | 5'-MeO, 6'-MeO | MeO | |
| 272 | (X-8) | 3-Cl, 5-$CH_3$ | Me | 5'-MeO, 6'-MeO | MeO | |
| 273 | (X-8) | 3-F, 5-MeO | Me | 5'-MeO, 6'-MeO | MeO | |
| 274 | (X-8) | 2-Cl, 3-$CF_3$, 6-$CF_3$ | Me | 5'-MeO, 6'-MeO | MeO | m.p. 154–158° C. |
| 275 | (X-8) | 3-$CF_3$, 6-$CF_3$ | Me | 5'-MeO, 6'-MeO | MeO | |
| 276 | (X-8) | 3-$CF_3$, 5-Me, 6-$CF_3$ | Me | 5'-MeO, 6'-MeO | MeO | |
| 277 | (X-8) | 3-$CF_3$, 5-Et, 6-$CF_3$ | Me | 5'-MeO, 6'-MeO | MeO | |
| 278 | (X-8) | 3-$CF_3$, 5-Allyl, 6-$CF_3$ | Me | 5'-MeO, 6'-MeO | MeO | |
| 279 | (X-8) | 3-$CF_3$, 5-n-Propyl, 6-$CF_3$ | Me | 5'-MeO, 6'-MeO | MeO | |
| 280 | (X-8) | 3-$CF_3$, 5-Propargyl, 6-$CF_3$ | Me | 5'-MeO, 6'-MeO | MeO | |
| 281 | (X-8) | 2-Cl, 3-$CF_3$, 5-$CF_3$, 6-Cl | Me | 5'-MeO, 6'-MeO | MeO | |
| 282 | (X-8) | 2-Cl, 3-$CF_3$, 5-$CF_3$ | Me | 5'-MeO, 6'-MeO | MeO | |

TABLE 36

| No. | Formula | $(X)_n$ | $R^1$ | $(R^2)_p$ | $R^3$ | Physical properties |
|---|---|---|---|---|---|---|
| 283 | (X-8) | 3-$CF_3$, 5-$CF_3$ | Me | 5'-MeO, 6'-MeO | MeO | |
| 284 | (X-9) | 3-Cl, 5-Cl, 6-Cl | Me | 5'-MeO, 6'-MeO | MeO | m.p. 97–99° C. |
| 285 | (X-9) | 3-F, 5-F, 6-F | Me | 5'-MeO, 6'-MeO | MeO | |
| 286 | (X-9) | 3-Br, 5-Br | Me | 5'-MeO, 6'-MeO | MeO | m.p. 114–117° C. |

The benzoylpyridine derivative represented by the formula (I) or its salt is useful as an active ingredient for a fungicide, particularly as an active ingredient for an agricultural and horticultural fungicide. As the agricultural and horticultural fungicide, it is effective for controlling diseases such as blast, brown spot or sheath blight of rice (*Oryza sativa*); powdery mildew, scab, rust, snow mold, loose smut, eyespot, leaf spot or glume blotch of barley (*Hordeum vulgare*); melanose or scab of citrus (Citrus); blossom blight, powdery mildew, Altenaria leaf spot or scab of apple (*Malus pumila*); scab or black spot of pear (*Pyrus serotina, Pyrus ussuriensis, Pyrus communis*); brown rot, scab or Fomitopsis rot of peach (*Prunus persica*); Anthracnose, ripe rot, powdery mildew or downy mildew of grape (*Vitis vinifera*); anthracnose or circular leaf spot of Japanese persimmon (*Diospyros kaki*); anthracnose, powdery mildew, gummy stem blight or downy mildew of cucurbit (*Cucumis melo*); early blight, leaf mold or late blight of tomato (*Lycopersicon esculentum*); leaf blight of cress (Brassica sp., Raphanus sp., etc); early blight or late blight of potato (*Solanum tuberosum*); powdery mildew of strawberry (*Fragaria chiloensis*); gray mold or stem rot of various crops. It shows an excellent controlling effect particularly on powdery mildew of barley and vegetables and rice blast. Further, it is also effective for controlling soil-borne diseases caused by phytopathogenic fungi such as Fusarium, Pythium, Rhizoctonia, Verticillium and Plasmodiophora.

The compound of the present invention may be used in combination with an agricultural adjuvant to formulate various preparations of the fungicide containing the compound, such as a dust, granules, a granular wettable powder, a wettable powder, an aqueous suspension, an oil suspension, a water soluble powder, an emulsifiable concentrate, an aqueous solution, a paste, an aerosol or a microdose dusting powder. The compound of the present invention may be formed into any preparation which is usually used in the agricultural and horticultural field so long as the purpose of the present invention is met. The adjuvant to be used for preparation may, for example, be a solid carrier such as diatomaceous earth, hydrated lime, calcium carbonate, talc, white carbon, kaolin, bentonite, a mixture of kaolinite and sericite, clay, sodium carbonate, sodium bicarbonate, glauber's salt, zeolite or starch; a solvent such as water, toluene, xylene, solvent naphtha, dioxane, acetone, isophorone, methyl isobutyl ketone, chlorobenzene, cyclohexane, dimethylsulfoxide, dimethylformamide, dimethylacetamide, N-methyl-2-pyrrolidone or an alcohol; an anionic surfactant or spreading agent such as a fatty acid salt, a benzoate, an alkyl sulfosuccinate, a dialkyl sulfosuccinate, a polycarboxylate, an alkyl sulfuric ester salt, an alkyl sulfate, an alkyl aryl sulfate, an alkyl diglycol ether sulfate, an alcohol sulfuric ester salt, an alkyl sulfonate, an alkyl aryl sulfonate, an aryl sulfonate, a lignin sulfonate, an alkyl diphenyl ether disulfonate, a polystyrene sulfonate, an alkyl phosphoric ester salt, an alkyl aryl phosphate, a styryl aryl phosphate, a polyoxyethylene alkyl ether sulfuric ester salt, a polyoxyethylene alkyl aryl ether sulfate, a polyoxyethylene alkyl aryl ether sulfuric ester salt, a polyoxyethylene alkyl ether phosphate, a polyoxyethylene alkyl aryl phosphoric ester salt or a salt of a naphthalene sulfonic acid formalin condensate; a non-ionic surfactant or spreading agent such as a sorbitan fatty acid ester, a glycerol fatty acid ester, a fatty acid polyglyceride, a fatty acid alcohol polyglycol ether, an acetylene glycol, an acetylene alcohol, an oxyalkylene block polymer, a polyoxyethylene alkyl ether, a polyoxyethylene alkyl aryl ether, a polyoxyethylene styryl aryl ether, a polyoxyethylene glycol alkyl ether, a polyoxyethylene fatty acid ester, a polyoxyethylene sorbitan fatty acid ester, a polyoxyethylene glycerol fatty acid ester, a polyoxyethylene hardened caster oil or a polyoxypropylene fatty acid ester; vegetable oil or mineral oil such as olive oil, kapok oil, caster oil, palm oil, camellia oil, coconut oil, sesame oil, corn oil, rice bran oil, peanut oil, cotton oil, soy bean oil, rape oil, linseed oil, tung oil or liquid paraffin. A known adjuvant may be selected from adjuvants which are known in the agricultural and horticultural field within a range of not departing from the object of the present invention. Further, an adjuvant which is usually used may also be employed, such as a bulking agent, a thickener, an anti-settling agent, a freeze proofing agent, a dispersion stabilizer, a crop injury-reducing agent or a mildewproofing agent. The blending proportion of the compound of the present invention to the adjuvant is generally from 0.005:99.995 to 95:5, preferably from 0.2:99.8 to 90:10. These formulations can be practically used either as they are or after they are diluted with a diluent such as water to predetermined concentrations and a spreading agent is added thereto as the case requires.

The concentration of the compound of the present invention varies depending upon the crop plant as the object, the way of application, the form of preparation or the dose, and hence cannot be generically determined. However, in the case of foliage treatment, the concentration of the compound as the active ingredient is generally from 0.1 to 10,000 ppm, preferably from 1 to 2,000 ppm. In the case of soil treatment, it is generally from 10 to 100,000 g/ha, preferably from 200 to 20,000 g/ha.

The preparation fungicide containing the compound of the present invention or a diluted product thereof can be applied by an application method which is commonly used, such as spreading (spreading, spraying, misting, atomizing, grain diffusing or application on water), soil application (such as mixing or irrigation) or surface application (such as coating, dust coating or covering). Further, it may be applied also by so-called ultra low volume. By this method, the preparation can contain 100% of the active ingredient.

The fungicide of the present invention may be mixed or used together with e.g. another agricultural chemical such as an insecticide, a miticide, a nematicide, a fungicide, an antiviral agent, an attractant, an herbicide or a plant growth regulator. In such a case, a still more excellent effect may be obtained in some cases.

Examples of the active ingredient compound (generic name; including compounds which are under application) of the insecticide, miticide or nematicide i.e. a pesticide of the above other agricultural chemicals, include organic phosphate type compounds such as Profenofos, Dichlorvos, Fenamiphos, Fenitrothion, EPN, Diazinon, Chlorpyrifos-methyl, Acephate, Prothiofos, Fosthiazate, Phosphocarb, Cadusafos and Dislufoton;

carbamate type compounds such as Carbaryl, Propoxur, Aldicarb, Carbofuran, Thiodicarb, Methomyl, Oxamyl, Ethiofencarb, Pirimicarb, Fenobucarb, Carbosulfan and Benfuracarb;

nelicetoxin derivatives such as Cartap and Thiocyclam;

organic chlorine type compounds such as Dicofol and Tetradifon;

organic metal type compounds such as Fenbutatin Oxide;

pyrethroid type compounds such as Fenvalerate, Permethrin, Cypermethrin, Deltamethrin, Cyhalothrin, Tefluthrin, Ethofenprox and Flufenprox;

benzoyl urea type compounds such as Diflubenzuron, Chlorfluazuron, Teflubenzuron and Flufenoxuron;

juvenile hormone-like compounds such as Methoprene;

pyridazinone type compounds such as Pyridaben;

pyrazole type compounds such as Fenpyroximate, Fipronil, Tebufenpyrad, Ethiprole, Tolefenpyrad and Acetoprole;

neonicotinoides such as Imidacloprid, Nitenpyram, Acetamiprid, Thiacloprid, Thiamethoxam, Clothianidin, Nidinotefuran and Dinotefuran;

hydrazine type compounds such as Tebufenozide, Methoxyfenozide and Chromafenozide;

pyridine type compounds such as Pyridaryl and Flonicamid;

tetronic acid type compounds such as Spirodiclofen;

strobilurin type compounds such as Fluacrypyrin;

dinitro type compounds, organosulfur compounds, urea type compounds, triazine type compounds, hydrozone type compounds and other compounds such as Buprofezin, Hexythiazox, Amitraz, Chlordimeform, Silafluofen, Triazamate, Pymetrozine, Pyrimidifen, Chlorfenapyr, Indoxacarb, Acequinocyl, Etoxazole, Cyromazine and 1,3-dichloropropene; AKD-1022 and IKA-2000. Further, the fungicide of the present invention may also be mixed or used together with a microbial pesticide such as a BT agent or an insect pathogenic virus agent or an antibiotic such as Avermectin, Milbemycin, Spinosad or Emamectin Benzoate.

Of these other agricultural chemicals, examples of the active ingredient compounds of the fungicides (generic name; including compounds which are under application) include pyrimidinamine type compounds such as Mepanipyrim, Pyrimethanil and Cyprodinil, pyridinamine type compound such as Fluazinam;

azole type compounds such as Triadimefon, Bitertanol, Triflumizole, Etaconazole, Propiconazole, Penconazole, Flusilazole, Myclobutanil, Cyproconazole, Terbuconazole, Hexaconazole, Furconazole-cis, Prochloraz, Metconazole, Epoxiconazole, Tetraconazole, Oxpoconazole fumarate and Sipconazole;

quinoxaline type compounds such as Quinomethionate;

dithiocarbamate type compounds such as Maneb, Zineb, Mancozeb, Polycarbamate, Metiram and Propineb;

organic chlorine type compounds such as Fthalide, Chlorothalonil and Quintozene;

imidazole type compounds such as Benomyl, Thiophanate-Methyl, Carbendazim and Cyazofamid;

cyanoacetamide type compounds such as Cymoxanil;

phenylamide type compounds such as Metalaxyl, Metalaxyl M, oxadixyl, Ofurace, Benalaxyl, Furalaxyl and Cyprofuram;

sulfenic acid type compounds such as Dichlofluanid;

copper type compounds such as Cupric hydroxide and Oxine Copper;

isoxazole type compounds such as Hydroxyisoxazole;

organophosphorus compounds such as Fosetyl-Al, Tolcofos-Methyl, S-benzyl O-diisopropylphosphorothioate, O-ethyl S,S-diphenylphosphorodithioate and aluminum ethyl hydrogen phosphonate;

N-halogenothioalkyl type compounds such as Captan, Captafol and Folpet;

dicarboxyimide type compounds such as Procymidone, Iprodione and Vinclozolin;

benzanilide type compounds such as Flutolanil, Mepronil and Zoxamid;

piperazine type compounds such as Triforine;

pyridine type compounds such as Pyrifenox;

carbionol type compounds such as Fenarimol and Flutriafol;

piperidine type compounds such as Fenpropidine;

morpholine type compounds such as Fenpropimorph;

organotin type compounds such as Fentin Hydroxide and Fentin Acetate;

urea type compounds such as Pencycuron;

cinnamic acid type compounds such as Dimethomorph;

phenyl carbamate type compounds such as Diethofencarb;

cyanopyrrole type compounds such as Fludioxonil and Fenpiclonil;

strobilurin type compounds such as Azoxystrobin, Kresoxim-Methyl, Metominofen, Triflouxystrobin, Picoxystrobin and Pyraclostrobin: (BAS 500F); oxazolidinone type compounds such as Famoxadone; thiazole carboxamide type compounds such as Ethaboxam;

silyl amide type compounds such as Silthiopham; aminoacid amidecarbamate type compounds such as Iprovalicarb and Benthiavalicarb; Imidazolidine type compounds such as fenamidone; hydroxyanilide type compounds such as Fenhexamid; benzene sulfonamide type compounds such as Flusulfamid; oxime ether type compounds such as Cyflufenamid; phenoxyamide type compounds such as Fenoxanil; triazole type compounds such as Simeconazole;

anthraquinone type compounds; crotonic acid type compounds; antibiotics and other compounds such as Isoprothiolane, Tricyclazole, Pyroquilon, Diclomezine, Pro. benazole, Quinoxyfen, Propamocarb Hydrochloride, Spiroxamine, Chloropicrin, Dazomet and Metam-sodium; and BJL-993, BJL-994, BAS-510, BAS-505, MTF-753 and UIBF-307.

Now, Test Examples of the agricultural and horticultural fungicides of the present invention will be described below. However, the present invention is by no means restricted thereto. In each test, the controlling index was determined on the basis of the following standards.

[Controlling Index]: [Degree of Disease Outbreak:Visual Observation]

5: No lesions nor sporogony recognizable

4: Area of lesions, number of lesions or area of sporogony is less than 10% of non-treated plot 3: Area of lesions, number of lesions or area of sporogony is less than 40% of non-treated plot 2: Area of lesions, number of lesions or area of sporogony is less than 70% of non-treated plot 1: Area of lesions, number of lesions or area of sporogony is at least 70% of non-treated plot Test Example 1

Tests on Preventive Effect Against Wheat Powdery Mildew

Wheat (cultivar: Norin-61-go) was cultivated in a polyethylene pot having a diameter of 7.5 cm, and when the wheat reached a one and a half-leaf stage, the wheat was sprayed with 10 ml of a drug solution having a predetermined concentration of the compound of the present invention by a spray gun. After the drug solution dried, the wheat was inoculated by spreading with conidiospore of fungi of powdery mildew, and the wheat was kept in a thermostatic chamber at 20° C. From 6 to 8 days after the inoculation, the area of sporogony was examined to determine the controlling index in accordance with the above evaluation standards. As a result, of the above compounds, compounds Nos. 1, 2, 8, 47, 58, 61, 62, 69, 73, 76, 77, 78, 83, 87, 91, 107, 110, 112, 114, 117, 119, 138, 250, 262 and 274 showed effects with a controlling index of 4 or above at a concentration of 500 ppm, and the compounds Nos. 3, 4, 5, 6, 7, 9, 10, 11, 13, 14, 18, 19, 23, 27, 30, 31, 32, 33, 34, 35, 36, 38, 40, 41, 43, 50, 51, 54, 55, 56, 59, 65, 72, 74, 75, 82, 84, 89, 90, 92, 93, 94, 99, 100, 101, 102, 103, 104, 105, 106, 108, 109, 111, 113, 118, 120, 121, 122, 123, 124, 133, 136, 142, 186, 187, 188, 189, 190, 191, 192, 193, 194, 199, 200, 210, 211, 213, 228, 243, 245, 249, 252, 254, 272, 287, 288, 289, 290, 291 and 292 showed effects with a controlling index of 4 or above at a concentration of 125 ppm.

Test Example 2

Test on Preventive Effect Against Rice Blast

Rice (cultivar: Nihonbare) was calculated in a polyethylene pot having a diameter of 7.5 cm, and when the rice reached a one and a half-leaf stage, the rice was sprayed with 10 ml of a drug solution having a predetermined concentration of the compound of the present invention by a spray gun. After the drug solution dried, the rice was sprayed and inoculated with a conidiospore suspension of fungi of rice blast, and the rice was kept in an inoculation box at 20° C. for 24 hours, and then kept in a thermostatic chamber at 20° C. From 6 to 11 days after the inoculation, the number of lesions was examined to determine the controlling index in accordance with the above evaluation standards. As a result, of the above compounds, the compounds Nos. 31, 56, 76, 90, 103 and 136 showed effects with a controlling index of 4 or above at a concentration of 500 ppm, and the compounds Nos. 50, 74, 75 and 102 showed effects with a controlling index of 4 or above at a concentration of 125 ppm.

Test Example 3

Test on Preventive Effect Against Eggplant Powdery Mildew

Eggplant (cultivar: Senryo-2-go) was cultivated in a polyethylene pot having a diameter of 7.5 cm, and when the eggplant reached a two-leaf stage, the eggplant was sprayed with 10 ml of a drug solution having a predetermined concentration of the compound of the present invention by a spray gun. After the drug solution dried, the eggplant was inoculated by spreading with conidiospore of fungi of eggplant powdery mildew, and the eggplant was kept in a thermostatic chamber at 20° C. 16 days after the inoculation, the area of sporogony was examined to determine the controlling index in accordance with the above evaluation standards. As a result, of the above compounds, compounds Nos. 1, 3, 5, 7, 92, 101 and 103 showed effects with a controlling index of 4 or above at a concentration of 500 ppm, and the compounds Nos. 9, 11, 55, 90 and 102 showed effects with a controlling index of 4 or above at a concentration of 125 ppm.

Test Example 4

Test on Preventive Effect Against Cucumber Powdery Mildew

Cucumber (cultivar: Suyo) was cultivated in a polyethylene pot having a diameter of 7.5 cm, and when the cucumber reached one and a half-leaf stage, the cucumber was sprayed with a 10 ml of a drug solution having a predetermined concentration of the compound of the present invention by a spray gun. After the drug solution dried, the cucumber was sprayed and inoculated with a conidiospore suspension of fungi of powdery mildew, and the cucumber was kept in a thermostatic chamber at 20° C. From 7 to 11 days after the inoculation, the area of sporogony was examined to determine the controlling index in accordance with the above evaluation standards. As a result, of the above compounds, the compound No. 98 showed effects with a controlling index of 4 or above at a concentration of 500 ppm, and compounds Nos. 1, 5, 7, 9, 55, 74, 90, 92, 93, 102, 103, 123 and 124 showed effects with a controlling index of 4 or above at a concentration of 125 ppm.

Now, Formulation Examples of the compounds of the present invention will be described below. However, the formulation dose, the dosage form or the like is by no means restricted to the following Examples.

Formulation Example 1

| | |
|---|---|
| (1) Compound of the present invention | 20 parts by weight |
| (2) Clay | 72 parts by weight |
| (3) Sodium lignin sulfonate | 8 parts by weight |

The above components are uniformly mixed to obtain a wettable powder.

Formulation Example 2

| | |
|---|---|
| (1) Compound of the present invention | 5 parts by weight |
| (2) Talc | 95 parts by weight |

The above components are uniformly mixed to obtain a dust.

Formulation Example 3

| | |
|---|---|
| (1) Compound of the present invention | 20 parts by weight |
| (2) N,N'-dimethylacetamide | 20 parts by weight |
| (3) Polyoxyethylene alkyl phenyl ether | 10 parts by weight |
| (4) Xylene | 50 parts by weight |

The above components are uniformly mixed and dissolved to obtain an emulsifiable concentrate.

Formulation Example 4

| | |
|---|---|
| (1) Clay | 68 parts by weight |
| (2) Sodium lignin sulfonate | 2 parts by weight |
| (3) Polyoxyethylene alkyl aryl sulfate | 5 parts by weight |
| (4) Fine silica | 25 parts by weight |

A mixture of the above components and the compound of the present invention are mixed in a weight ratio of 4:1 to obtain a wettable powder.

Formulation Example 5

| | |
|---|---|
| (1) Compound of the present invention | 50 parts by weight |
| (2) Oxylated polyalkylphenyl phosphate-triethanolamine | 2 parts by weight |
| (3) Silicone | 0.2 part by weight |
| (4) Water | 47.8 parts by weight |

The above components are uniformly mixed and pulverized to obtain a stock solution, and

| | |
|---|---|
| (5) Sodium polycarboxylate | 5 parts by weight |
| (6) Anhydrous sodium sulfate | 42.8 parts by weight | are further added thereto, followed by uniform mixing, granulation and drying to obtain a granular wettable powder.

Formulation Example 6

| | |
|---|---|
| (1) Compound of the present invention | 5 parts by weight |
| (2) Polyoxyethylene octylphenyl ether | 1 part by weight |
| (3) Phosphate of polyoxyethylene | 0.1 part by weight |
| (4) Particulate calcium carbonate | 93.9 parts by weight |

The above components (1) to (3) are preliminarily mixed uniformly and diluted with a proper amount of acetone, the diluted mixture is sprayed on the component (4), and acetone is removed to obtain granules.

Formulation Example 7

| | |
|---|---|
| (1) Compound of the present invention | 2.5 parts by weight |
| (2) N-methyl-2-pyrrolidone | 2.5 parts by weight |
| (3) Soybean oil | 95.0 parts by weight |

The above components are uniformly mixed and dissolved to obtain an ultra low volume formulation.

Formulation Example 8

| | | |
|---|---|---|
| (1) | Compound of the present invention | 20 parts by weight |
| (2) | Oxylated polyalkylphenol phosphate triethanolamine | 2 parts by weight |
| (3) | Silicone | 0.2 part by weight |
| (4) | Xanthan gum | 0.1 part by weight |
| (5) | Ethylene glycol | 5 parts by weight |
| (6) | Water | 72.7 parts by weight |

The above components are uniformly mixed and pulverized to obtain an aqueous suspension.

Industrial Applicability

As mentioned above, the benzoylpyridine derivative represented by the formula (I) or its salt has excellent effects as an active ingredient of a fungicide.

What is claimed is:

1. A fungicide which contains (a) a benzoylpyridine derivative represented by the formula (I) or its salt as an active ingredient:

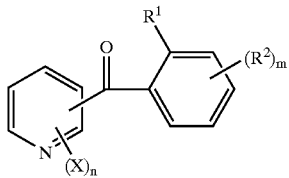

(I)

wherein X is a halogen atom, a nitro group, an optionally substituted alkoxy group, an optionally substituted aryloxy group, an optionally substituted cycloalkoxy group, a hydroxyl group, an optionally substituted hydrocarbon group, an optionally substituted alkylthio group, a cyano group, a carboxyl group which may be esterified or amidated, or an optionally substituted amino group; n is 1, 2, 3 or 4; $R^1$ is an optionally substituted alkyl group; $R^2$ is an optionally substituted alkyl group, an optionally substituted alkoxy group, an optionally substituted aryloxy group, a an optionally substituted cycloalkoxy group or a hydroxyl group; and m is 1, 2, 3 or 4, provided that when m is at least 2, $R^2$ may contain an oxygen atom to form a condensed ring (with the proviso that compounds where the pyridine ring is substituted by a benzoyl group at the 2-position; the pyridine ring is substituted by an alkoxy group, a hydroxyl group or a benzyloxy group at the 3-position; and n is 1, m is 1 or 2, are excluded), and wherein when the derivative is a 3-benzoylpyridine compound, at least one $R^2$ is substituted at the 5' position, and (b) at least one agricultural adjuvant, or
(c) at least one agricultural chemical, or
(b) and (c).

2. The fungicide according to claim 1, wherein X is a halogen atom, a nitro group, an optionally substituted alkoxy group, an optionally substituted aryloxy group, an optionally substituted cycloalkoxy group, a hydroxyl group, an optionally substituted hydrocarbon group, an optionally substituted alkylthio group, a cyano group or an optionally substituted amino group.

3. The fungicide according to claim 1, wherein m is 2, 3 or 4.

4. The fungicide according to claim 1, wherein $R^1$ is an alkyl group, and $R^2$ is an alkyl group, an alkoxy group or a hydroxyl group.

5. A benzoylpyridine derivative or its salt which is represented by the formula (I'):

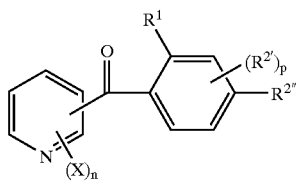

(I')

wherein X is a halogen atom, a nitro group, an optionally substituted alkoxy group, an optionally substituted aryloxy group, an optionally substituted cycloalkoxy group, a hydroxyl group, an optionally substituted hydrocarbon group, an optionally substituted alkylthio group, a cyano group, a carboxyl group which may be esterified or amidated, or an optionally substituted amino group; n is 1, 2, 3 or 4; $R^1$ is an optionally substituted alkyl group wherein the substituents are selected from the group consisting of an aryl, and aryloxy, hydroxyl, nitro, nitroxy, a halogen, a haloalkoxy, a cycloalkyl, amino, an atlkylthio and cyano; $R^{2'}$ is an optionally substituted alkyl group, an optionally substituted alkoxy group, an optionally substituted aryloxy group, an optionally substituted cycloalkoxy group or a hydroxyl group, p is 1, 2 or 3, and $R^{2''}$ is an optionally substituted alkoxy group or a hydroxyl group, provided that at least two of $R^{2'}$ and $R^{2''}$ may contain an oxygen atom to form a condensed ring (with the proviso that compounds where the pyridine ring is substituted by a benzoyl group at the 2-position; the pyridine ring is substituted by an alkoxy group, a hydroxyl group or a benzyloxy group at the 3-position; and n is 1, p is 1, are excluded), and wherein when the derivative is a 3-benzoylpyridine compound, at least one $R^{2'}$ is substituted at the 5' position.

6. The benzoylpyridine derivative or its salt according to claim 5, which is represented by the formula (I''):

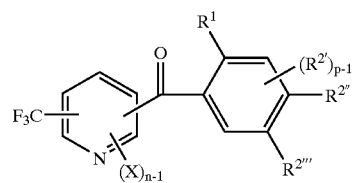

(I'')

wherein X is a halogen atom, a nitro group, an optionally substituted alkoxy group, an optionally substituted aryloxy group, an optionally substituted cycloalkoxy group, an optionally substituted hydrocarbon group, an optionally substituted alkylthio group, a cyano group, a carboxyl group which may be esterified or amidated, or an optionally substituted amino group; n is 1, 2, 3 or 4; $R^1$ is an alkyl group; $R^{2'}$ is an optionally substituted alkyl group, an optionally substituted alkoxy group, an optionally substituted aryloxy group or an optionally substituted cycloalkoxy group, p is 1, 2 or 3, is an optionally substituted alkoxy group, and $R^{2'''}$ is an optionally substituted alkoxy group and takes the place of the $R^{2'}$ that is substituted at the 5' position.

7. The benzoylpyridine derivative or its salt according to claim 5, which is represented by the formula (I'''):

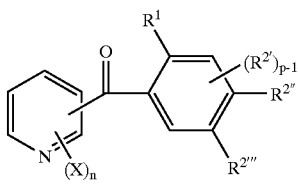

(I''')

wherein X is a halogen atom, an optionally substituted alkoxy group, an alkyl group, a $CF_3$ group or an alkylthio group; n is 1, 2, 3 or 4; $R^1$ is an alkyl group; $R^{2'}$ is an optionally substituted alkyl group, an optionally substituted alkoxy group or an optionally substituted cycloalkoxy group; p is 1, 2 or 3; $R^{2''}$ is an optionally substituted alkoxy group, and $R^{2'''}$ is an optionally substituted alkoxy group and takes the place of the $R^{2'}$ that is substituted at the 5' position.

8. The benzoylpyridine derivative or its salt according to claim 5, which is represented by the formula (I''''):

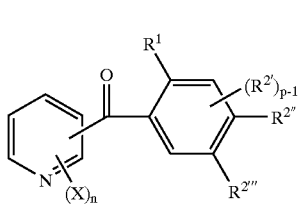

(I'''')

wherein X is a halogen atom, an alkoxy group, an alkyl group, a $CF_3$ group or an alkylthio group; n is 1, 2 or 3; $R^1$ is an alkyl group; $R^{2'}$ is an alkoxy group; p is 1, 2 or 3, $R^{2''}$ is an alkoxy group, and $R^{2'''}$ is an alkoxy group and takes the place of the $R^{2'}$ that is substituted at the 5' position.

9. The benzoylpyridine derivative or its salt according to claim 8, which is represented by the formula (I'''''):

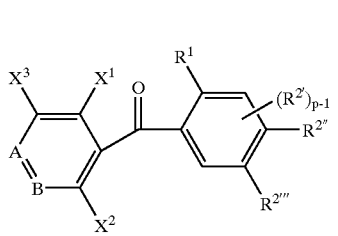

(I''''')

wherein B is —$CX^4$= when A is —N=; B is —N= when A is
—CH=; each of $X^1$ $X^2$ which are independent of each other, is a halogen atom, an alkoxy group, an alkyl group, a $CF_3$ group or an alkylthio group; $X^4$ is a hydrogen atom, a halogen atom, an alkoxy group, an alkyl group, a $CF_3$ group or an alkylthio group; $X^4$ is a hydrogen atom, a halogen atom, an alkoxy group, an alkyl group, a $CF_3$ group or an alkylthio group; $R^1$ is an alkyl group; $R^{2'}$ is an alkoxy group; p is 1, 2 or 3; $R^{2''}$ is an alkoxy group, and $R^{2'''}$ is an alkoxy group and takes the place of the $R^{2'}$ that is substituted at the 5' position.

10. A fungicide which contains (a) the benzoylpyridine derivative represented by the formula (I') or its salt as defined in claim 5 as an active ingredient, and (b) at least one agricultural adjuvant, or (c) at least one agricultural chemical, or (b) and (c).

11. A phenylpyridyl methanol which is represented by the formula (X'):

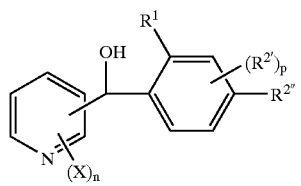

(X')

wherein X is a halogen atom, a nitro group, an optionally substituted alkoxy group, an optionally substituted aryloxy group, an optionally substituted cycloalkoxy group, a hydroxyl group, an optionally substituted hydrocarbon group, an optionally substituted alkylthio group, a cyano group, a carboxyl group which may be esterified or amidated, or an optionally substituted amino group: n is 1, 2, 3 or 4; $R^1$ is an optionally substituted alkyl group; $R^{2'}$ is an optionally substituted alkyl group, a an optionally substituted alkoxy group, an optionally substituted aryloxy group, an optionally substituted cycloalkoxy group or a hydroxyl group, p is 1, 2 or 3, and $R^{2''}$ an optionally substituted alkoxy group or a hydroxyl group, provided that at least two of $R^{2'}$ and $R^{2''}$ may contain an oxygen atom to form a condensed ring (with the proviso that compounds where the pyridine ring is substituted by a α-hydroxy benzyl group at the 2-position; the pyridine ring is substituted by an alkoxy group, a hydroxyl group or a benzyloxy group at the 3-position; and n is 1, p is 1, are excluded).

12. The phenylpyridyl methanol according to claim 11, which is represented by the formula (X''):

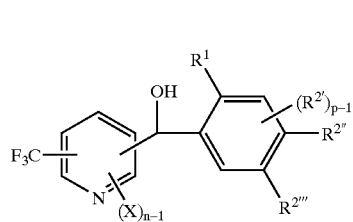

(X'')

wherein X is a halogen atom, a nitro group, an optionally substituted alkoxy group, an optionally substituted aryloxy group, an optionally substituted cycloalkoxy group, an optionally substitued hydrocarbon group, an optionally substituted alkylthio group, a cyano group, a carboxyl group which may be esterified or amidated, or a an optionally substituted amino group; n is 1, 2, 3 or 4; $R^1$ is an alkyl group; $R^{2'}$ is an optionally substituted alkyl group, an optionally substituted alkoxy group, an optionally substituted aryloxy group or an optionally substituted cycloalkoxy group, p is 1, 2 or 3, and each of $R^{2''}$ and $R^{2'''}$ is an optionally substituted alkoxy group.

13. The phenylpyridyl methanol according to claim 11, which is represented by the formula (X'''):

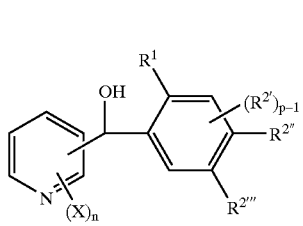

(X''')

wherein X is a halogen atom, an optionally substituted alkoxy group, an alkyl group, a $CF_3$ group or an alkylthio group; n is 1, 2, 3 or 4; $R^1$ is an alkyl group; $R^{2'}$ is an optionally substituted alkyl group, an optionally substituted alkoxy group or an optionally substituted cycloalkoxy group; p is 1, 2 or 3; and each of $R^{2''}$ and $R^{2'''}$ is an optionally substituted alkoxy group.

14. The phenylpyridyl methanol according to claim 11, which is represented by the formula (X''''):

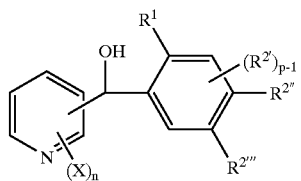

(X'''')

wherein X is a halogen atom, an alkoxy group, an alkyl group, a CF₃ group or an alkylthio group; n is 1, 2 or 3; R¹ is an alkyl group; R2' is an alkoxy group; p is 1, 2 or 3; and each of R2" and R2''' is an alkoxy group.

15. The phenylpyridyl methanol according to claim 14, which is represented by the formula (X'''''):

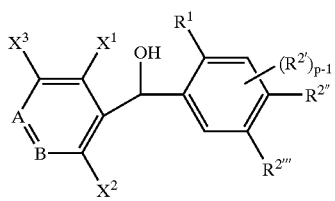

(X''''')

wherein B is —CX⁴= when A is —N=; B is —N= when A is
—CH=; each of X¹ and X² which are independent of each other, is a halogen atom, an alkoxy group, an alkyl group, a CF₃ group or an alkylthio group; X³ is a hydrogen atom, a halogen atom, an alkoxy group, an alkyl group, a CF₃ group or an alkylthio group; X⁴ is a hydrogen atom, a halogen atom, an alkoxy group, an alkyl group, a CF₃ group or an alkylthio group; R¹ is an alkyl group; R2' is an alkoxy group; p is 1, 2 or 3; and each of R2" and R2''' is an alkoxy group.

16. A method comprising applying a benzoylpyridine derivative represented by the formula (I) or its salt, in fungicidal effective amounts to a plant in need thereof:

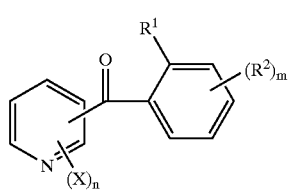

(I)

wherein X is a halogen atom, a nitro group, an optionally substituted alkoxy group, an optionally substituted aryloxy group, an optionally substituted cycloalkoxy group, a hydroxyl group, an optionally substituted hydrocarbon group, an optionally substituted alkylthio group, a cyano group, a carboxyl group which may be esterified or amidated, or an optionally substituted amino group; n is 1, 2, 3 or 4; R¹ is an optionally substituted alkyl group; R² is an optionally substituted alkyl group, an optionally substituted alkoxy group, an optionally substituted aryloxy group, an optionally substituted cycloalkoxy group or a hydroxyl group; and m is 1, 2, 3 or 4, provided that when m is at least 2, R² may contain an oxygen atom to form a condensed ring (with the proviso that compounds where the pyridine ring is substituted by a benzoyl group at the 2-position; the pyridine ring is substituted by an alkoxy group, a hydroxyl group or a benzyloxy group at the 3-position; and n is 1, m is 1 or 2, are excluded), wherein when the derivative is a 3-benzoylpyridine compound, at least one R² is substituted at the 5' position.

17. A process for producing a benzoylpyridine derivative represented by the formula (I') or its salt:

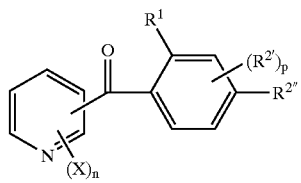

(I')

{wherein X is a halogen atom, a nitro group, an optionally substituted alkoxy group, an optionally substituted aryloxy group, an optionally substituted cycloalkoxy group, a hydroxyl group, an optionally substituted hydrocarbon group, an optionally substituted alkylthio group, a cyano group, a carboxyl group which may be esterified or amidated, or an optionally substituted amino group; n is 1, 2, 3 or 4; R¹ is an optionally substituted alkyl group; R2' is an optionally substituted alkyl group, an optionally substituted alkoxy group, an optionally substituted aryloxy group, an optionally substituted cycloalkoxy group or a hydroxyl group; and p is 1, 2 or 3; R2" is an optionally substituted alkoxy group or a hydroxyl group; provided that at least two of R2' and R2" may contain an oxygen atom to form a condensed ring (with the proviso that compounds where the pyridine ring is substituted by a benzoyl group at the 2-position; the pyridine ring is substituted by an alkoxy group, a hydroxyl group or a benzyloxy group at the 3-position; and n is 1, p is 1, are excluded), and wherein when the derivative is a 3-benzoylpyridine compound, at least one R2' is substituted at the 5' position}, which process comprises reacting a substituted benzaldehyde represented by the formula (VI-1):

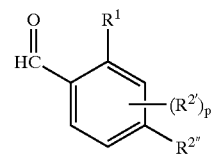

(VI-1)

(wherein R¹, R2', R2" and p are as defined above) and a metal salt of a substituted pyridine derivative represented by the formula (VII-1):

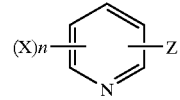

(VII-1)

(wherein X is as defined above, and Z is a metal atom or a composite salt thereof) to produce phenylpyridyl methanol represented by the formula (X):

(X)

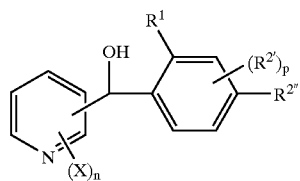

(wherein X, n, p, $R^1$, $R^{2'}$, and $R^{2''}$ are as defined above, with a proviso as in formula (I')), and oxidizing it.

18. A process for producing a benzoylpyridine derivative represented by the formula (I') or its salt:

(I')

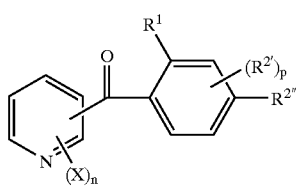

{wherein X is a halogen atom, a nitro group, an optionally substituted alkoxy group, an optionally substituted aryloxy group, an optionally substituted cycloalkoxy group, a hydroxyl group, an optionally substituted hydrocarbon group, an optionally substituted alkylthio group, a cyano group, a carboxyl group which may be esterified or amidated, or an optionally substituted amino group; n is 1, 2, 3 or 4; $R^1$ is an optionally substituted alkyl group; $R^{2'}$ is an optionally substituted alkyl group, an optionally substituted alkoxy group, an optionally substituted aryloxy group, an optionally substituted cycloalkoxy group or a hydroxyl group; p is 1, 2 or 3; and $R^{2''}$ is an optionally substituted alkoxy group or a hydroxyl group; provided that when p is at least 2, two of $R^{2'}$ and $R^{2''}$ may contain an oxygen atom to form a condensed ring (with the proviso that compounds where the pyridine ring is substituted by a benzoyl group at the 2-position; the pyridine ring is substituted by an alkoxy group, a hydroxyl group or a benzyloxy group at the 3-position; and n is 1, p is 1 or 2, are excluded), and wherein when the derivative is a 3-benzoylpyridine compound, at least one $R^{2'}$ is substituted at the 5' position}, which process comprises reacting a metal salt of a substituted benzene derivative represented by the formula (VI-2):

(VI-2)

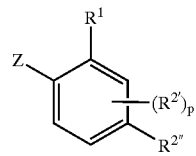

(wherein $R^1$, $R^{2'}$, $R^{2''}$ and p are as defined above, and Z is a metal atom or a composite salt thereof) and a substituted pyridyl aldehyde represented by the formula (VII-2):

(VII-2)

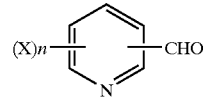

(wherein X is as defined above) to produce phenylpyridyl methanol represented by the formula (X):

(X)

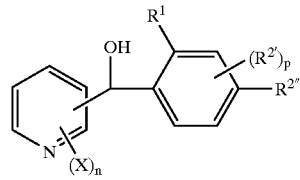

(wherein X, n, p, $R^1$, $R^{2'}$, and $R^{2''}$ are as defined above with a proviso as in formula (I')), and oxidizing it.

* * * * *